US008080560B2

(12) United States Patent
Statham et al.

(10) Patent No.: US 8,080,560 B2
(45) Date of Patent: *Dec. 20, 2011

(54) IMMUNE RESPONSE MODIFIER FORMULATIONS CONTAINING OLEIC ACID AND METHODS

(75) Inventors: Alexis S. Statham, Woodbury, MN (US); Robert J. Nelson, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1451 days.

This patent is subject to a terminal disclaimer.

(21) Appl. No.: 11/276,324

(22) Filed: Feb. 24, 2006

(65) Prior Publication Data

US 2007/0123558 A1 May 31, 2007

(51) Int. Cl.
*A01N 43/42* (2006.01)
*A01N 43/52* (2006.01)
(52) U.S. Cl. ........................ 514/290; 514/393
(58) Field of Classification Search ................. 514/290, 514/393
See application file for complete search history.

(56) References Cited

U.S. PATENT DOCUMENTS

| | | | |
|---|---|---|---|
| 24,906 A | 12/1960 | Ulrich | |
| 3,700,674 A | 10/1972 | Diehl et al. | |
| 4,013,665 A | 3/1977 | Crenshaw et al. | |
| 4,052,393 A | 10/1977 | Treuner | |
| 4,191,767 A | 3/1980 | Warner, Jr. et al. | |
| 4,197,403 A | 4/1980 | Warner, Jr. et al. | |
| 4,411,893 A | 10/1983 | Johnson et al. | |
| 4,601,856 A | 7/1986 | Suzuki et al. | |
| 4,686,125 A | 8/1987 | Johnston et al. | |
| 4,689,338 A | 8/1987 | Gerster | |
| 4,695,465 A | 9/1987 | Kigasawa et al. | |
| 4,698,348 A | 10/1987 | Gerster | |
| 4,722,941 A | 2/1988 | Eckert et al. | |
| 4,746,515 A | 5/1988 | Cheng et al. | |
| 4,751,087 A | 6/1988 | Wick | |
| 4,863,970 A | 9/1989 | Patel et al. | |
| 4,908,389 A | 3/1990 | Mahjour et al. | |
| 4,929,624 A | 5/1990 | Gerster | |
| 5,008,110 A | 4/1991 | Benecke et al. | |
| 5,238,944 A | 8/1993 | Wick et al. | |
| 5,266,575 A | 11/1993 | Gerster | |
| 5,268,376 A | 12/1993 | Gester | |
| 5,300,291 A | 4/1994 | Sablotsky et al. | |
| 5,346,905 A | 9/1994 | Gerster | |
| 5,352,784 A | 10/1994 | Nikolaides et al. | |
| 5,389,640 A | 2/1995 | Gerster et al. | |
| 5,446,153 A | 8/1995 | Lindstrom et al. | |
| 5,472,982 A | 12/1995 | Suzuki | |
| 5,482,936 A | 1/1996 | Lindstrom | |
| 5,532,030 A | 7/1996 | Hirose et al. | |
| 5,736,553 A | 4/1998 | Wick et al. | |
| 5,756,747 A | 5/1998 | Gerster et al. | |
| 5,919,815 A | 7/1999 | Bradley et al. | |
| 5,939,090 A | 8/1999 | Beaurline et al. | |
| 6,039,969 A | 3/2000 | Tomai et al. | |
| 6,103,697 A | 8/2000 | Bergstrand et al. | |
| 6,110,929 A | 8/2000 | Gerster et al. | |
| 6,194,425 B1 | 2/2001 | Gerster et al. | |
| 6,200,592 B1 | 3/2001 | Tomai et al. | |
| 6,210,712 B1 | 4/2001 | Edgren et al. | |
| 6,245,776 B1 | 6/2001 | Skwierczynski et al. | |
| 6,267,957 B1 | 7/2001 | Green et al. | |
| 6,331,539 B1 | 12/2001 | Crooks et al. | |
| 6,376,669 B1 | 4/2002 | Rice et al. | |
| 6,425,776 B1 | 7/2002 | Fredl | |
| 6,451,810 B1 | 9/2002 | Coleman et al. | |
| 6,498,261 B1 | 12/2002 | Ewbank et al. | |
| 6,525,064 B1 | 2/2003 | Dellaria et al. | |
| 6,541,485 B1 | 4/2003 | Crooks et al. | |
| 6,545,016 B1 | 4/2003 | Dellaria et al. | |
| 6,545,017 B1 | 4/2003 | Dellaria et al. | |
| 6,559,182 B1 | 5/2003 | Purcell | |
| 6,562,363 B1 | 5/2003 | Mantelle et al. | |
| 6,573,273 B1 | 6/2003 | Crooks et al. | |
| 6,638,528 B1 | 10/2003 | Kanios | |
| 6,656,938 B2 | 12/2003 | Crooks et al. | |
| 6,660,735 B2 | 12/2003 | Crooks et al. | |
| 6,660,747 B2 | 12/2003 | Crooks et al. | |
| 6,664,260 B2 | 12/2003 | Charles et al. | |
| 6,664,264 B2 | 12/2003 | Dellaria et al. | |
| 6,664,265 B2 | 12/2003 | Crooks et al. | |
| 6,667,312 B2 | 12/2003 | Bonk et al. | |
| 6,670,372 B2 | 12/2003 | Charles et al. | |
| 6,677,347 B2 | 1/2004 | Crooks et al. | |

(Continued)

FOREIGN PATENT DOCUMENTS

EP 0 107 455 B1 7/1986

(Continued)

OTHER PUBLICATIONS

Croda, Inc. Product Literature, "SUPER REFINED® OLEIC ACID NF" *Pharmaceutical & Nutritional*, PN-38, (2002), pp. 1-4. (Croda, Inc.: Parisippany, NY).

Naik et al., "Mechanism of oleic acid-induced skin penetration enhancement in vivo in humans," *Journal of Controlled Release* 37 (1995) pp. 299-306.

Green et al., "In vitro and in vivo enhancement of skin permeation with oleic and lauric acids," *International Journal of Pharmaceutics*, 48 (1988), pp. 103-111.

Yamashita et al., "Analysis of in vivo skin penetration enhancement by oleic acid based on a two-layer diffusion model with polar and nonpolar routes in the stratum corneum," *International Journal of Pharmaceutics* 117 (1995), pp. 173-179.

(Continued)

*Primary Examiner* — Sreeni Padmanabhan
*Assistant Examiner* — Renee Claytor
(74) *Attorney, Agent, or Firm* — Edwards Wildman Palmer LLP; Peter J. Manso; William J. Daley, Jr.

(57) ABSTRACT

Pharmaceutical formulations and methods including an immune response modifier (IRM) compound and an oleic acid component are provided where stability is improved by using oleic acid have low polar impurities such as peroxides.

132 Claims, No Drawings

U.S. PATENT DOCUMENTS

| | | |
|---|---|---|
| 6,677,348 B2 | 1/2004 | Heppner et al. |
| 6,677,349 B1 | 1/2004 | Griesgraber |
| 6,683,088 B2 | 1/2004 | Crooks et al. |
| 6,756,382 B2 | 6/2004 | Coleman et al. |
| 6,797,718 B2 | 9/2004 | Dellaria et al. |
| 6,803,420 B2 | 10/2004 | Cleary et al. |
| 6,818,650 B2 | 11/2004 | Griesgraber |
| 7,056,528 B1 | 6/2006 | Bracht et al. |
| 7,504,114 B1 | 3/2009 | Kurita et al. |
| 2002/0128345 A1 | 9/2002 | Paul |
| 2003/0026794 A1 | 2/2003 | Fein |
| 2003/0059471 A1 | 3/2003 | Compton et al. |
| 2003/0072814 A1 | 4/2003 | Maibach et al. |
| 2003/0096012 A1 | 5/2003 | Besse et al. |
| 2003/0124191 A1 | 7/2003 | Besse et al. |
| 2003/0170308 A1 | 9/2003 | Cleary et al. |
| 2003/0199538 A1 | 10/2003 | Skwierczynski |
| 2003/0211163 A1 | 11/2003 | Chong |
| 2004/0089855 A1 | 5/2004 | Oommen et al. |
| 2004/0091491 A1 | 5/2004 | Kedl et al. |
| 2004/0132766 A1 | 7/2004 | Griesgraber |
| 2004/0147543 A1 | 7/2004 | Hays et al. |
| 2004/0176367 A1 | 9/2004 | Griesgraber et al. |
| 2004/0192585 A1 | 9/2004 | Owens et al. |
| 2004/0242770 A1 | 12/2004 | Feldstein et al. |
| 2005/0037030 A1 | 2/2005 | Kumar et al. |
| 2005/0175630 A1 | 8/2005 | Raz et al. |
| 2005/0201959 A1 | 9/2005 | David |
| 2005/0276842 A1 | 12/2005 | Zhang et al. |
| 2005/0281772 A1 | 12/2005 | Bromley et al. |
| 2006/0024243 A1 | 2/2006 | Arkin et al. |
| 2006/0034779 A1 | 2/2006 | Arkin et al. |
| 2006/0039931 A1 | 2/2006 | Scheiwe et al. |
| 2007/0167479 A1 | 7/2007 | Busch et al. |
| 2007/0196457 A1 | 8/2007 | Zhang et al. |

FOREIGN PATENT DOCUMENTS

| | | |
|---|---|---|
| EP | 0 187 705 A2 | 7/1986 |
| EP | 0 394 026 | 9/1993 |
| EP | 0 582 581 B1 | 2/1994 |
| EP | 1 512 685 B1 | 3/2005 |
| HU | P0002103 | 10/2000 |
| JP | 61-00297 | 1/1986 |
| JP | 62-148449 | 7/1987 |
| JP | 05-246948 | 9/1993 |
| JP | 07-138145 | 5/1995 |
| PT | 76045 | 12/1985 |
| PT | 76145 | 12/1985 |
| PT | 76145 B | 12/1985 |
| WO | 88/09676 | 12/1988 |
| WO | WO-88/09676 | 12/1988 |
| WO | WO-92/15582 A1 | 9/1992 |
| WO | WO-01/06829 A2 | 2/2001 |
| WO | WO-01/07009 A1 | 2/2001 |
| WO | WO-2004/024126 A1 | 3/2004 |
| WO | WO-2004/037201 A2 | 5/2004 |
| WO | WO 2005/020995 | 3/2005 |
| WO | WO-2005/020999 A1 | 3/2005 |
| WO | WO-2005/067897 A1 | 7/2005 |
| WO | WO-2005/074894 A1 | 8/2005 |
| WO | WO-2005/079143 A2 | 9/2005 |
| WO | WO 2005/089317 | 9/2005 |
| WO | WO-2006/074046 A2 | 7/2006 |
| WO | WO-2006/074046 A3 | 7/2006 |
| WO | WO-2008/010963 A2 | 1/2008 |
| WO | WO-2008/010963 A3 | 1/2008 |

OTHER PUBLICATIONS

Yamane et al., "Effects of terpenes and oleic acid as skin penetration enhancers towards 5-fluorouracil as assessed with time; permeation, partitioning and differential scanning calorimetry," *International Journal of Pharmaceutics* 116, (1995), pp. 237-251.

Meshulam et al., "Transdermal Penetration of Physostigmine: Effects of Oleic Acid Enhancer," *Drug Development Research* 28 (1993), pp. 510-515.

Kim et al., "Enhanced Bioavilability of Aceclofenac Using Solid Dispersions: Bioequivalence Test of Capsule and Tablet with Different Doses in Human Volunteers," *Controlled Release Society 29th Annual Meeting Proceedings*, (2002), pp. 730-731.

MacGregor et al., "Influence of lipolysis on drug absorption from the gastro-intestinal tract," *Advanced Drug Delivery Reviews* 25 (1997), pp. 33-46.

N. Thorgaard Pedersen, "Fat Digestion Tests," *Digestion* 37:suppl. 1 (1987), pp. 25-34.

Bonte et al., "Experimental Myocardial Imaging with I-Labeled Oleic Acid," *Work in Progress, Radiology* 108: (1973), pp. 195-196.

Abbasi et al., "Base Induced Cyclization of Some Quinolines. Formation of Fused Nitrogen Heterocyclic Ring System" *Monatshefte für Chemie* (1980)111:963-969.

Abbasi et al., "Base Induced Cyclization of Some Quinolines. Formation of Fused Nitrogen Hetercyclic Ring System," *Chemical Abstracts* (1981) 94:47216.

Bachman, et al., "Synthesis of Substituted Quinolylamines. Derivatives of 4-Amino-7-Chloroquinoline," *Journal of Organic Chemistry*, 15(1950), pp. 1278-1284.

Backeberg et al., "The Reaction between Hydrazine Hydrate and 4-Chloroquinoline Derivatives.", *Journal of Chemistry Society* (1938)pp. 972-977.

Backeberg, O.G. "The Reaction between Phenylhdrazine and 4-Chloroquinoline Derivatives, and the Preparation of the Corresponding 4-Benezeneazo-and 4-Amino-compounds.", *Journal of Chemical Society*(1938), pp. 1083-1087.

Baranov et al., "Imidazo[4,5-c]quinolines" *Chemical Abstracts* (1976), 85:94362.

Bartek et al., "Percutaneous Absorption, In Vitro, Animal Models in Dermatology, with Relevance to Human Dermatopharmacology and Dermatotoxicology," *Churchill Livingtone* (New York) (1975), pp. 103-120.

Berényi et al., "Ring Transformation of Condensed Dihydro-astriazines," *Journal of Heterocyclic Chemistry*, vol. 18 (1981), pp. 1537-1540.

Bhargava, H.N., Ph.D., "The Present Status of Formulation of Cosmetic Emulsions," *Drug Development and Industrial Pharmacy*, 13(13)(1987), pp. 2363-2387.

Billmeyer, Fred W., "Polymer Chains and Their Characterization," *Textbook of Polymer Science* (1971), pp. 84-85.

Chien et al., "Transdermal Controlled Administration of Indomethacin. I. Enhancement of Skin Permeability," *Pharmaceutical Research*, vol. 5:2 (1988), pp. 103-106.

Cohen et al., "Penetration of 5-Fluorouracil in Excised Skin " *The Journal of Investigative Dermatoloy*, 62:5 (1974) pp. 507-509.

Cooper, Eugene. R., "Increased Skin Permeabilty for Lipophilic Molecules," *Journal of Pharmaceutical Sciences*, vol. 73, No. 8 (1984), pp. 1153-1156.

Green, et al., "Rapid, Quantitative, Semiautomated Assay for Virus-Induced and Immune Human Interferons," *Journal of Clinical Microbiology*, 12:3 (1980), pp. 433-438.

Jain et al., "Chemical and Pharmacological Investiations of Some w-Substituted Alkylamino-3-aminopyridines," *Journal of Medicinal Chemistry*, (1986) vol. 11: 87-92.

Kern, et al., "Treatment of Experimental Herpesvirus Infections with Phosphonoformate and Some Comparisons with Phosphonoacetate," *Antimocrobial Agents and Chemotherapy*, 14:6 (1978), pp. 817-823.

Koenigs et al., "Uber die Einwirkung von Hydrazin en auf 4-Chlorchinaldin," *Chimische Berichte*, (1947), 80:143-149.

Lachman et al., "The Theory and Practice of Industrial Pharmacy," *The Theory and Practice of Industrial Pharmacy. Lea & Febiger*, Philadelphia, 2nd Edition (1976), pp. 220-229.

Loftsson et al., "The Effect of Vehicle Additives on the Transdermal Delivery of Nitroglycerin," *Pharmaceutical Research*, vol. 4:5 (1987), pp. 436-437.

Overall, Jr. et al., "Activity of Human Recombinant and Lymphoblastoid Interferons in Human and Heterologous Cell Lines," *Journal of Interferon Research* (1984), vol. 4, pp. 529-533.

Stanberry, et. al., "Genital Herpes in Guinea Pigs: Pathogenesis of the Primary Infection and Description of Recurrent Disease," *The Journal of Infectious Diseases*, 146:3(1982), pp. 397-404.

Stoughton, Richard B., "Animal Models for in Vitro Percutaneous Absorption," *Animal Models in Dermatology Relevance to Human*

*Dermatopharmacology and Dermatotoxicology* Churchill Livingstone (New York) (1975), pp. 121-132.

Stoughton, Richard B., "Vasoconstrictor Activity and Percutaneous Absorption of Glucocorticosteroids," *Archives of Dermatology*, vol. 99 (1969), pp. 753-756.

Surrey et al., "The Synthesis of Some 3-Nitro- and 3-Amino-4-dialklaminoalklaminoquinoline Derivatives," *Journal of the American Chemical Society* (Jun. 1951) 73:2413-2416.

The Delphion Inegrated View: INPADOC Record, Bouman et al., "Preparation and purification of lovastatin derivatives used as hydroxymethyl glutaryl coenzyme A reductase inhibitors—comprises adjusting pH, removing cells used to prepare them, heating and contacting with resin," Acession No. 1998-570544/200225.

The Delphion Integrated View: INPADOC Record, Ciba Geigy AG, "Imidazo (4,5-c) quinoline prepn.—consists of reduction of a lower alkylene di:oxy cpd. through reaction with ammonia, etc.), or cpd. of forumla (II) is reacted with e.g. ammonia," Accession No. 1984-168891/198427.

Weissberger & Taylor, "Quinolines," *The Chemistry of Heterocyclic Compounds*, (1977) pp. 562-563.

Yu et al., "Percutaneous Absorption of Nicardipine and Ketorolac in Rhesus Monkeys," *Pharmaceutical Research*, vol. 5:7(1998), pp. 457-462.

*The 3M Story: A Century of Innovation*, "No Risk, No Reward—'Patient Money'," (2002) Chapter 6, pp. 77-93.

Barnes, Kirsty, "Croda presents new high purity excipients", in-Pharma Technologist.com, http://www.in-pharmatechnologist.com, 4 pages.

Chronological History of Lipid Science, History of lipids (1669-2008), http://www.cyberlipid.org/history1.htm, pp. 1-55.

Fatty Acid and Dimer Acid Market Research (China), Abstract, Market Publishers Know Your Market, http://marketpublishers.com, 9 pages.

Goliath, "Super refined oleic acid available from Croda", *Household & Personal Products Industry*, http://goliath.ecnext.com, pp. 1-2.

Google News Archive Search, "Timeline for of Refining oleic acid", and "Production and Market of Fatty Acid and Dimer Acid in China", http://news.google.com/archivesearch; http://www.marketresearch.com/product/display, 5 pages.

IDES, "The Plastics Web", http://www.ides.com/grades/Barex_grades.htm, 10 pages.

Olive Oil Definitions—The Olive Oil source, http://www.oliveoilsource.com/definitions.htm, 8 pages.

USP Material Safety Data Sheet, "Oleic Acid", Catalog No. 1478130, U.S. Pharmacopeia, (2004) pp. 1-6.

What is Oleic Acid? wiseGEEK, http://www.wisegeek.com/what-is-oleic-acid.htm, 3 pages.

Croda, "Super Refined Oleic Acid NF", Pharmaceutical & Nutritional, PN-38, 2002, pp. 1-4.

Chollet et al., "Development of a Topically Active Imiquimod Formulation", Pharmaceutical Development and Technology, 4(1), pp. 35-43 (1999).

Goliath et al., "Super Refined Oleic Acid Available from Croda", Household & Personal Products Industry, http://goliath.ecnext.com, pp. 1-2.

USP Material Safety Data Sheet, "Oleic Acid", Catalog No. 1478130, U.S. Pharmacopeia, pp. 1-6 (2004).

USP Certificate—Oleic Acid LOT F0E001, Cat. No. 1478130.

Amendment and Response to U.S. Appl. No. 07/845,323 (U.S. Patent No. 5,238,944) with Affidavit of Dr. Berge.

2008 USPC Official Dec. 1, 2007-Apr. 30, 2008—NF Monographs: Oleic Acid.

Household & Personal Products Industry: Super refined oleic acid available from Croda, Feb. 1, 2003, Rodman Publicaions.

Lashmar, et al. J. Pharm. Pharmacol. 1989, Topical Application of Penetration Enhancers to the Skin of Nude Mice: A Histopathological Study; vol. 41:118-121.

Croda—Super Refined Oleic Acid NF.

U.R. Hengge et al., "Topical Immunomodulators—Progress Towards Treating Inflammation, Infection and Cancer", *The LANCET Infectious Diseases*, vol. 1, pp. 189-198 (2001).

U.R. Hengge et al., "Errata", *The LANCET Infectious Diseases*, vol. 2, p. 259 (2002).

Lashmar, et al. J. Pharm. Pharmacol. 1989, "Topical Application of Penetration Enhancers to the Skin of Nude Mice: A Histopathological Study"; vol. 41:118-121.

Loftsson, et al. Pharmaceutical Res. 1987, "The Effect of Vehicle Additives on the Transdermal Delivery of Nitroglycerin"; vol. 4(5): 436-437.

Martindale's "The Extra Pharmacopoeia", $28^{th}$ edition, p. 1067 (1982).

Chollet et al. "Development of a Topically Active Imiquimod Formulation", *Pharmaceutical Development and Technology*, 4(1), pp. 35-43 (1999).

International Search Report and Written Opinion of the International Searching Authority for International Application No. PCT/US06/49517.

Feb. 23, 2010 Complaint with supporting documents; *Graceway Pharmaceuticals, LLC and 3M Innovative Properties Company v. Perrigo Company et al.*, U.S. District Court, District of New Jersey, Case No. 2:22-av-00001.

Feb. 28, 2010 Nordsiek Declaration with Exhibits A & B; *Graceway Pharmaceuticals, LLC and 3M Innovative Properties Company v. Perrigo Company et al.*, U.S. District Court, District of New Jersey, Case No. 2:22-av-00001.

Feb. 28, 2010 Nordsiek Exhibit D; *Graceway Pharmaceuticals, LLC and 3M Innovative Properties Company v. Perrigo Company et al.*, U.S. District Court, District of New Jersey, Case No. 2:22-av-00001.

Feb. 28, 2010 Novak Exhibit 6; *Graceway Pharmaceuticals, LLC and 3M Innovative Properties Company v. Perrigo Company et al.*, U.S. District Court, District of New Jersey, Case No. 2:22-av-00001.

Feb. 28, 2010 Novak Exhibits 7-8; *Graceway Pharmaceuticals, LLC and 3M Innovative Properties Company v. Perrigo Company et al.*, U.S. District Court, District of New Jersey, Case No. 2:22-av-00001.

Feb. 28, 2010 Novak Exhibits 9-10; *Graceway Pharmaceuticals, LLC and 3M Innovative Properties Company v. Perrigo Company et al.*, U.S. District Court, District of New Jersey, Case No. 2:22-av-00001.

Feb. 28, 2010 TRO Brief; *Graceway Pharmaceuticals, LLC and 3M Innovative Properties Company v. Perrigo Company et al.*, U.S. District Court, District of New Jersey, Case No. 2:22-av-00001.

Mar. 1, 2010 Redacted Memorandum in Opposition; *Graceway Pharmaceuticals, LLC and 3M Innovative Properties Company v. Perrigo Company et al.*, U.S. District Court, District of New Jersey, Case No. 2:10-cv-937-SDW-MCA.

Mar. 1, 2010 Banker Declaration; *Graceway Pharmaceuticals, LLC and 3M Innovative Properties Company v. Perrigo Company et al.*, U.S. District Court, District of New Jersey, Case No. 2:10-cv-00937 (WJM-MF).

Mar. 1, 2010 Colucci Declaration; *Graceway Pharmaceuticals, LLC and 3M Innovative Properties Company v. Perrigo Company et al.*, U.S. District Court, District of New Jersey, Case No. 2:10-cv-00937 (WJM-MF).

Mar. 1, 2010 Palmieri Declaration; *Graceway Pharmaceuticals, LLC and 3M Innovative Properties Company v. Perrigo Company et al.*, U.S. District Court, District of New Jersey, Case No. 2:10-cv-00937 (WJM-MF).

Mar. 1, 2010 Romito Declaration; *Graceway Pharmaceuticals, LLC and 3M Innovative Properties Company v. Perrigo Company et al.*, U.S. District Court, District of New Jersey, Case No. 2:10-cv-00937 (WJM-MF).

Mar. 2, 2010 Hearing Transcript; *Graceway Pharmaceuticals, LLC and 3M Innovative Properties Company v. Perrigo Company et al.*, U.S. District Court, District of New Jersey, Case No. 2:10-cv-00937 (WJM-MF).

Mar. 5, 2010 Reply in Support of TRO; *Graceway Pharmaceuticals, LLC and 3M Innovative Properties Company v. Perrigo Company et al.*, U.S. District Court, District of New Jersey, Case No. 2:10-cv-00937 (WJM-MF).

Mar. 19, 2010 Nycomed's Answer and Counterclaims; *Graceway Pharmaceuticals, LLC and 3M Innovative Properties Company v. Perrigo Company et al.*, U.S. District Court, District of New Jersey, Case No. 2:10-cv-00937 (WJM-MF).

Mar. 23, 2010 Declaration of Keith A. Johnson with Exhibit A; *Graceway Pharmaceuticals, LLC and 3M Innovative Properties Company v. Perrigo Company et al.*, U.S. District Court, District of New Jersey, Case No. 2:10-cv-00937 (WJM-MF).

Mar. 23, 2010 Declaration of Peter J. Manso*Graceway Pharmaceuticals, LLC and 3M Innovative Properties Company v. Perrigo Company et al.*, U.S. District Court, District of New Jersey, Case No. 2:10-cv-00937 (WJM-MF).

Mar. 23, 2010 First Declaration of Marc B. Brown with Exhibits A-C; *Graceway Pharmaceuticals, LLC and 3M Innovative Properties Company v. Perrigo Company et al.*, U.S. District Court, District of New Jersey, Case No. 2:10-cv-00937 (WJM-MF).

Mar. 23, 2010 Plaintiff's Memorandum of Law for Preliminary Injunction; *Graceway Pharmaceuticals, LLC and 3M Innovative Properties Company v. Perrigo Company et al.*, U.S. District Court, District of New Jersey, Case No. 2:10-cv-00937 (WJM-MF).

Mar. 23, 2010 Second Declaration of Marc B. Brown with Exhibits A to B; *Graceway Pharmaceuticals, LLC and 3M Innovative Properties Company v. Perrigo Company et al.*, U.S. District Court, District of New Jersey, Case No. 2:10-cv-00937 (WJM-MF).

Mar. 23, 2010 Exhibits C to D of Second Declaration of Marc B. Brown; *Graceway Pharmaceuticals, LLC and 3M Innovative Properties Company v. Perrigo Company et al.*, U.S. District Court, District of New Jersey, Case No. 2:10-cv-00937 (WJM-MF).

Mar. 23, 2010 Exhibits E to K to Second Declaration of Marc B. Brown; *Graceway Pharmaceuticals, LLC and 3M Innovative Properties Company v. Perrigo Company et al.*, U.S. District Court, District of New Jersey, Case No. 2:10-cv-00937 (WJM-MF).

Apr. 19, 2010 Declaration of Andrew Zhou; *Graceway Pharmaceuticals, LLC and 3M Innovative Properties Company v. Perrigo Company et al.*, U.S. District Court, District of New Jersey, Case No. 2:10-cv-00937 (WJM-MF).

Apr. 19, 2010 Declaration of Arthur Steiner; *Graceway Pharmaceuticals, LLC and 3M Innovative Properties Company v. Perrigo Company et al.*, U.S. District Court, District of New Jersey, Case No. 2:10-cv-00937 (WJM-MF).

Apr. 19, 2010 Nycomed's Opposition to PI; *Graceway Pharmaceuticals, LLC and 3M Innovative Properties Company v. Perrigo Company et al.*, U.S. District Court, District of New Jersey, Case No. 2:10-cv-00937 (WJM-MF).

Apr. 19, 2010 Second Declaration of Gilbert Banker with Exhibits A and B; *Graceway Pharmaceuticals, LLC and 3M Innovative Properties Company v. Perrigo Company et al.*, U.S. District Court, District of New Jersey, Case No. 2:10-cv-00937 (WJM-MF).

Apr. 19, 2010 Second Declaration of James Romito; *Graceway Pharmaceuticals, LLC and 3M Innovative Properties Company v. Perrigo Company et al.*, U.S. District Court, District of New Jersey, Case No. 2:10-cv-00937 (WJM-MF).

Apr. 19, 2010 Second Declaration of James Palmieri, III; *Graceway Pharmaceuticals, LLC and 3M Innovative Properties Company v. Perrigo Company et al.*, U.S. District Court, District of New Jersey, Case No. 2:10-cv-00937 (WJM-MF).

Apr. 26, 2010 Wiseman Declaration with Exhibits A-K; *Graceway Pharmaceuticals, LLC and 3M Innovative Properties Company v. Perrigo Company et al.*, U.S. District Court, District of New Jersey, Case No. 2:10-cv-00937 (WJM-MF).

Apr. 26, 2010 Redacted PI Reply Brief; *Graceway Pharmaceuticals, LLC and 3M Innovative Properties Company v. Perrigo Company et al.*, U.S. District Court, District of New Jersey, Case No. 2:10-cv-00937 (WJM-MF).

Chollet, J.L. et al., "Crystal Formation by Drug-Excipient Interaction in a Topical Imiquimod Formulation," 1998 AAPS Annual Meeting.

Jun. 10, 2010 Opinion on Preliminary Injunction; *Graceway Pharmaceuticals, LLC and 3M Innovative Properties Company v. Perrigo Company et al.*, U.S. District Court, District of New Jersey, Case No. 2:10-cv-00937 (WJM-MF).

Jun. 10, 2010 Opinion on Rule 11 Motion; *Graceway Pharmaceuticals, LLC and 3M Innovative Properties Company v. Perrigo Company et al.*, U.S. District Court, District of New Jersey, Case No. 2:10-cv-00937 (WJM-MF).

Pacer Docket Sheets as of Dec. 28, 2010; *Graceway Pharmaceuticals, LLC and 3M Innovative Properties Company v. Perrigo Company et al.*, U.S. District Court, District of New Jersey, Case No. 2:10-cv-00937 (WJM-MF).

Joint Claim Construction and Prehearing Statement ; *Graceway Pharmaceuticals, LLC and 3M Innovative Properties Company v. Perrigo Company et al.*, U.S. District Court, District of New Jersey, Case No. 2:10-cv-00937, Nov. 29, 2010.

Sugisaka et al., "The Physicochemical Properties of Imiquimod, the First Imidazoquinoline Immune Response Modifier", *Pharmaceutical Research*, 14(11), Abtract # 3030, p. S475 (1997).

Chollet et al., "The Effect of Temperature on the Solubility of Imiquimod in Isostearic Acid", *Pharmaceutical Research*, 14(11), Abstract # 3031, p. S475 (1997).

Li et al., "Solubility Behavior of Imiquimod in Alkanoic Acids", *Pharmaceutical Research*, 14(11), Abstract # 3019, p. S475 (1997).

*Fragrance Journal*, 5(6), Issue No. 27, pp. 28-35 (Nov. 25, 1977).

*Yusi*, 35(2), 406th Issue, pp. 57-61 (Feb. 15, 1982).

*Fine Chemical*, 16(13), pp. 12-17 (Aug. 1, 1987).

*Fine Chemical*, 16(14), pp. 14-21 (Aug. 15, 1987).

*Fragrance Journal*, 19(8), Issue No. 125, p. 1 (Aug. 15, 1991).

*Fragrance Journal*, 19(8), Issue No. 125, pp. 12-22 (Aug. 15, 1991).

*Fragrance Journal*, 19(8), Issue No. 125, pp. 70-74 (Aug. 15, 1991).

*Fragrance Journal*, 21(7), Issue No. 148, pp. 25-35 (Jul. 15, 1993).

*Fragrance Journal*, 23(4), Issue No. 170, pp. 105-118 (Apr. 15, 1995).

*Fragrance Journal*, Special Issue No. 16, vol.No. 219, pp. 19-30 (Feb. 20, 1999).

*Chemical Engineering of Japan*, 67(4), pp. 233-235 (Apr. 5, 2003).

The Work of Dow Pharmaceutical Sciences in 2004; MM0001824.

The Work of Dow Pharmaceutical Sciences in 2004; MM0001835-1836.

The Work of Dow Pharmaceutical Sciences in 2004; MM0001842.

Nissan Extra Series, High-Purity Unsaturated Fatty Acids, NOF Corporation, available since at least 1984 (Extra Olein).

"Extra Pure Unsaturated Fatty Acids," Parfums Cosmetiques Aromes, No. 75:79-80 (Jun.-Jul. 1987).

Mar. 8, 2010 Opinion on Temporary Restraining Order; *Graceway Pharmaceuticals, LLC and 3M Innovative Properties Company v. Perrigo Company et al.*, U.S. District Court, District of New Jersey, Case No. 2:10-cv-00937 (WJM-MF).

Nycomed's Invalidity Contention Disclosure, USDC, D. New Jersey, Civil Action No. 2:10cv937, Sep. 7, 2010.

Nycomed's Revised Invalidity Contention Disclosure, USDC, D. New Jersey, Civil Action No. 2:10cv937, Oct. 8, 2010.

Physician's Desk Reference, 53 Edition, with Aldara Label Information Excerpt (1999).

Aldara Label/Package Insert (Dec. 2001).

Aldara Label/Package Insert (Mar. 2007).

Aldara Label/Package Insert (Apr. 2009).

Aldara Label/Package Insert (Apr. 2009).

Pacer Docket Sheets as of Nov. 23, 2010; *Graceway Pharmaceuticals, LLC and 3M Innovative Properties Company v. Perrigo Company et al.*, U.S. District Court, District of New Jersey, Case No. 2:10-cv-00937 (WJM-MF).

IMMUNE RESPONSE MODIFIER FORMULATIONS CONTAINING OLEIC ACID AND METHODS

CROSS-REFERENCE TO RELATED APPLICATIONS

This application claims benefit of U.S. provisional application 60/636,916, filed Dec. 17, 2004, and Ser. No. 11/303,659 filed Dec. 16, 2005 now abandoned, the contents of which are hereby incorporated by reference.

FIELD OF THE INVENTION

The present invention relates to pharmaceutical formulations for the topical or transdermal delivery of immunomodifying drugs.

BACKGROUND

There has been a major effort in recent years, with significant success, to discover new drug compounds that act by stimulating certain key aspects of the immune system, as well as by suppressing certain other aspects. These compounds, referred to herein as immune response modifiers (IRMs), appear to act through immune system mechanisms known as toll-like receptors to induce selected cytokine biosynthesis. They may be useful for treating a wide variety of diseases and conditions. For example, certain IRMs may be useful for treating viral diseases (e.g., human papilloma virus, hepatitis, herpes), neoplasias (e.g., basal cell carcinoma, squamous cell carcinoma, actinic keratosis, melanoma), and TH2-mediated diseases (e.g., asthma, allergic rhinitis, atopic dermatitis), and are also useful as vaccine adjuvants.

Many of the IRM compounds are small organic molecule imidazoquinoline amine derivatives (see, e.g., U.S. Pat. No. 4,689,338), but a number of other compound classes are known as well (see, e.g., U.S. Pat. Nos. 5,446,153, 6,194,425, and 6,110,929) and more are still being discovered.

One of these IRM compounds, known as imiquimod, has been commercialized in a topical formulation, ALDARA, for the treatment of actinic keratosis, basal cell carcinoma, or anogenital warts associated with human papillomavirus.

Pharmaceutical formulations containing IRM compounds are disclosed in U.S. Pat. Nos. 5,238,944; 5,939,090; and 6,425,776; European Patent 0 394 026; and U.S. Patent Publication 2003/0199538.

Although some of the beneficial effects of IRMs are known, the ability to provide therapeutic benefit via topical application of an IRM compound for treatment of a particular condition at a particular location may be hindered by a variety of factors. These factors include: irritation of the skin to which the formulation is applied; formulation wash away; insolubility of the IRM compound in the formulation; chemical degradation of the IRM compound and/or other ingredients, physical instability of the formulation (e.g., separation of components, thickening, precipitation/agglomerization of active ingredient, and the like); poor permeation; and undesired systemic delivery of topical IRM formulations if not intended to be transdermal.

Accordingly, there is a continuing need for new and/or improved IRM formulations.

SUMMARY

It has now been found that, while oleic acid can be used to solublize IRMs, even difficult to formulate, highly insoluble IRMs, formulations comprising an IRM compound in combination with oleic acid can suffer from impaired stability. Somewhat surprisingly, addition of greater amounts of antioxidants to the formulation does not solve the problem. However, it has been found that utilizing an oleic acid component having reduced amounts of polar impurities, such as peroxides, aldehydes, alcohols, and ketones in a formulation containing an IRM can reduce the formation of impurities and thereby provide improved formulation stability. Instability is an important issue for pharmaceutical formulations and can reduce the shelf life of a product or jeopardize regulatory approvability.

It has been discovered that the stability of a formulation containing an IRM compound and oleic acid can be improved by utilizing an oleic acid component that is free of or contains low amounts of polar impurities, such as peroxides, aldehydes, alcohols, and ketones. Although not intending to be bound to any particular theory or mechanism, it is hypothesized that the higher amounts of polar impurities present in the oleic acid component can react with the IRM compound, thereby destabilizing the formulation and increasing the rate of formation of impurities derived from the IRM compound.

In one aspect, the present invention provides a pharmaceutical formulation comprising a therapeutically effective amount of an immune response modifier (IRM) compound and a pharmaceutically acceptable vehicle including an oleic acid component, wherein the formulation is substantially free of polar impurities introduced by the oleic acid component.

In another aspect, the present invention provides a pharmaceutical formulation comprising: a therapeutically effective amount of an IRM compound and a pharmaceutically acceptable vehicle including an oleic acid component, wherein the oleic acid component has a peroxide value no greater than 5.

In another aspect, the present invention provides a pharmaceutical formulation comprising: a therapeutically effective amount of an IRM compound and a pharmaceutically acceptable vehicle including an oleic acid component, wherein the oleic acid component is at least 80% oleic acid.

The present invention also provides methods.

In one aspect, the present invention provides a method of stabilizing a pharmaceutical formulation comprising a therapeutically effective amount of an immune response modifier (IRM) compound and oleic acid by using an oleic acid component that is substantially free of polar impurities.

In one aspect, the present invention provides a method of stabilizing a pharmaceutical formulation comprising a therapeutically effective amount of an IRM compound and oleic acid by using an oleic acid component with a peroxide value no greater than 5.

In one aspect, the present invention provides a method of stabilizing a pharmaceutical formulation comprising a therapeutically effective amount of an IRM compound and oleic acid by using an oleic acid component that is at least 80% oleic acid.

In another aspect, the present invention provides methods for treating disease, including but not limited to the group comprising actinic keratosis, basal cell carcinoma, genital warts, peri-anal warts, malignant melanoma, and molloscum contagiosum. In another aspect, the present invention provides methods to induce cytokine biosynthesis. In another aspect, the present invention provides methods to induce interferon biosynthesis.

A number of additional embodiments can be described as follows:

1. A pharmaceutical formulation comprising:
   a therapeutically effective amount of an immune response modifier (IRM) compound selected from the group consisting of imidazoquinoline amines, tetrahydroimidazoquinoline amines, imidazopyridine amines, 6,7-fused cycloalkylimidazopyridine amines, 1,2-bridged imidazoquinoline amines, imidazonaphthyridine amines, tetrahydroimidazonaphthyridine amines, oxazoloquinoline amines, thiazoloquinoline amines, oxazolopyridine amines, thiazolopyridine amines, oxazolonaphthyridine amines, thiazolonaphthyridine amines, 1H-imidazo dimers fused to pyridine amines, quinoline amines, tetrahydroquinoline amines, naphthyridine amines, or tetrahydronaphthyridine amines, and combinations thereof; and
   a pharmaceutically acceptable vehicle including an oleic acid component, wherein the formulation is substantially free of polar impurities introduced by the oleic acid component.

2. A pharmaceutical formulation comprising:
   a therapeutically effective amount of an IRM compound selected from the group consisting of imidazoquinoline amines, tetrahydroimidazoquinoline amines, imidazopyridine amines, 6,7-fused cycloalkylimidazopyridine amines, 1,2-bridged imidazoquinoline amines, imidazonaphthyridine amines, tetrahydroimidazonaphthyridine amines, oxazoloquinoline amines, thiazoloquinoline amines, oxazolopyridine amines, thiazolopyridine amines, oxazolonaphthyridine amines, thiazolonaphthyridine amines, 1H-imidazo dimers fused to pyridine amines, quinoline amines, tetrahydroquinoline amines, naphthyridine amines, or tetrahydronaphthyridine amines, and combinations thereof; and
   a pharmaceutically acceptable vehicle including an oleic acid component, wherein the oleic acid component has a peroxide value no greater than 5.

3. A pharmaceutical formulation comprising:
   a therapeutically effective amount of an IRM compound selected from the group consisting of imidazoquinoline amines, tetrahydroimidazoquinoline amines, imidazopyridine amines, 6,7-fused cycloalkylimidazopyridine amines, 1,2-bridged imidazoquinoline amines, imidazonaphthyridine amines, tetrahydroimidazonaphthyridine amines, oxazoloquinoline amines, thiazoloquinoline amines, oxazolopyridine amines, thiazolopyridine amines, oxazolonaphthyridine amines, thiazolonaphthyridine amines, 1H-imidazo dimers fused to pyridine amines, quinoline amines, tetrahydroquinoline amines, naphthyridine amines, or tetrahydronaphthyridine amines, and combinations thereof; and
   a pharmaceutically acceptable vehicle including an oleic acid component, wherein the oleic acid component is at least 80% oleic acid.

4. A formulation as in any one of the preceding embodiments wherein the IRM compound is selected from the group consisting of amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, 6-, 7-, 8-, or 9-aryl, heteroaryl, aryloxy or arylalkyleneoxy substituted imidazoquinoline amines, imidazoquinoline diamines, amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, thioether substituted tetrahydroimidazoquinoline amines, tetrahydroimidazoquinoline diamines, amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, thioether substituted imidazopyridine amines, and combinations thereof.

5. A formulation as in any one of embodiments 1 through 3 wherein the IRM compound is an imidazonaphthyridine amine.

6. A formulation as in any one of embodiments 1 through 3 and 5 wherein the IRM compound is 2-methyl-1-(2-methylpropyl)-1H-imidazo[4,5-c][1,5]naphthyridin-4-amine.

7. A formulation as in any one of embodiments 1 through 3 wherein the IRM compound is 1-(2-methylpropyl)-1H-imidazo[4,5-c]quinolin-4-amine.

8. A formulation as in any one of the preceding embodiments wherein the IRM compound is present in an amount of at least 3% by weight, based on the total weight of the formulation.

9. A formulation as in any one of the preceding embodiments wherein the IRM compound is present in an amount of at least 5% by weight, based on the total weight of the formulation.

10. A formulation as in any one of the preceding embodiments wherein the oleic acid component is present in an amount of at least 15% by weight based on the total weight of the formulation.

11. A formulation as in any one of the preceding embodiments wherein the oleic acid component is present in an amount of at least 20% by weight based on the total weight of the formulation.

12. A formulation as in any one of the preceding embodiments wherein the oleic acid component is present in an amount of at least 25% by weight based on the total weight of the formulation.

13. A formulation as in any one of the preceding embodiments wherein the oleic acid component has been purified by chromatography prior to use in the formulation.

14. A formulation as in any one of the preceding embodiments wherein the oleic acid component is plant-derived.

15. A formulation as in any one of the preceding embodiments wherein the formulation includes at least one fatty acid other than oleic acid or isostearic acid.

16. A formulation as in any one of the preceding embodiments wherein the formulation includes less than 3% isostearic acid by weight based on the total weight of the formulation.

17. A formulation as in any one of the preceding embodiments wherein the formulation further comprises an antioxidant.

18. A formulation as in any one of the preceding embodiments further comprising an antioxidant, wherein the antioxidant is butylated hydroxyl toluene or butylated hydroxyanisole.

19. A formulation of any one of the preceding embodiments further comprising water.

20. A formulation of any one of the preceding embodiments further comprising a preservative system.

21. A formulation of any one of the preceding embodiments further comprising an emulsifier.
22. A method of stabilizing a pharmaceutical formulation comprising a therapeutically effective amount of an immune response modifier (IRM) compound selected from the group consisting of imidazoquinoline amines, tetrahydroimidazoquinoline amines, imidazopyridine amines, 6,7-fused cycloalkylimidazopyridine amines, 1,2-bridged imidazoquinoline amines, imidazonaphthyridine amines, tetrahydroimidazonaphthyridine amines, oxazoloquinoline amines, thiazoloquinoline amines, oxazolopyridine amines, thiazolopyridine amines, oxazolonaphthyridine amines, thiazolonaphthyridine amines, 1H-imidazo dimers fused to pyridine amines, quinoline amines, tetrahydroquinoline amines, naphthyridine amines, or tetrahydronaphthyridine amines, and combinations thereof; and oleic acid by using an oleic acid component that is substantially free of polar impurities.
23. A method of stabilizing a pharmaceutical formulation comprising a therapeutically effective amount of an IRM compound selected from the group consisting of imidazoquinoline amines, tetrahydroimidazoquinoline amines, imidazopyridine amines, 6,7-fused cycloalkylimidazopyridine amines, 1,2-bridged imidazoquinoline amines, imidazonaphthyridine amines, tetrahydroimidazonaphthyridine amines, oxazoloquinoline amines, thiazoloquinoline amines, oxazolopyridine amines, thiazolopyridine amines, oxazolonaphthyridine amines, thiazolonaphthyridine amines, 1H-imidazo dimers fused to pyridine amines, quinoline amines, tetrahydroquinoline amines, naphthyridine amines, or tetrahydronaphthyridine amines, and combinations thereof; and oleic acid by using an oleic acid component with a peroxide value no greater than 5.
24. A method of stabilizing a pharmaceutical formulation comprising a therapeutically effective amount of an IRM compound selected from the group consisting of imidazoquinoline amines, tetrahydroimidazoquinoline amines, imidazopyridine amines, 6,7-fused cycloalkylimidazopyridine amines, 1,2-bridged imidazoquinoline amines, imidazonaphthyridine amines, tetrahydroimidazonaphthyridine amines, oxazoloquinoline amines, thiazoloquinoline amines, oxazolopyridine amines, thiazolopyridine amines, oxazolonaphthyridine amines, thiazolonaphthyridine amines, 1H-imidazo dimers fused to pyridine amines, quinoline amines, tetrahydroquinoline amines, naphthyridine amines, or tetrahydronaphthyridine amines, and combinations thereof; and oleic acid by using an oleic acid component that is at least 80% oleic acid.
25. The method as in any one of embodiments 22 through 24 wherein the IRM compound is selected from the group consisting of: amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, 6-, 7-, 8-, or 9-aryl, heteroaryl, aryloxy, or arylalkyleneoxy substituted imidazoquinoline amines, imidazoquinoline diamines, amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, thioether substituted tetrahydroimidazoquinoline amines, tetrahydroimidazoquinoline diamines, amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, thioether substituted imidazopyridine amines, and combinations thereof.
26. The method as in any one of embodiments 22 through 24 wherein the IRM compound is an imidazonaphthyridine amine.
27. The method as in any one of embodiments 22 through 24 and 26 wherein the IRM compound is 2-methyl-1-(2-methylpropyl)-1H-imidazo[4,5-c][1,5]naphthyridin-4-amine.
28. The method as in any one of embodiments 22 through 24 wherein the IRM compound is 1-(2-methylpropyl)-1H-imidazo[4,5-c]quinolin-4-amine.
29. A method of treating actinic keratosis, the method comprising applying a formulation of any one of embodiments 1 through 21 to the skin of a subject.
30. A method of treating basal cell carcinoma, the method comprising applying a formulation of any one of embodiments 1 through 21 to the skin of a subject.
31. A method of treating genital warts, the method comprising applying a formulation of any one of embodiments 1 through 21 to the skin or mucosal surface of a subject.
32. A method of treating peri-anal warts, the method comprising applying a formulation of any one of embodiments 1 through 21 to the skin or mucosal surface of a subject.
33. A method of treating molloscum contagiosum, the method comprising applying a formulation of any one of embodiments 1 through 21 to the skin of a subject.
34. A method of inducing cytokine biosynthesis, the method comprising applying a formulation of any one of embodiments 1 through 21 to the skin or mucosal surface of a subject.
35. A method of inducing interferon biosynthesis, the method comprising applying a formulation of any one of embodiments 1 through 21 to the skin or mucosal surface of a subject.
36. A method of treating malignant melanoma, the method comprising applying a formulation of any one of the preceding embodiments 1 through 21 to the skin of a subject.

The term "substantially free" is used to indicate that the amount present in the composition or formulation is below the level that causes degradation of the active pharmaceutical agent, such that the formulation is unsuitable for pharmaceutical usage, after storage for 4 months at 40° C. at 75% relative humidity. The term can also be used to describe a composition containing less than 10%, less than 5%, less than 1%, or less than 0.1% by weight of a given substance.

The term "polar impurities" includes, but is not limited to peroxides, aldehydes, ketones, alcohols, metal ions, and/or substances that cause degradation of the active pharmaceutical agent.

The term "oleic acid component" is used to describe a preformulation source or composition of matter containing oleic acid, and may include other fatty acids in addition to oleic acid, including but not limited to: myristic acid, palmitic acid, palmitoleic acid, margaric acid, isostearic acid, stearic acid, linoleic acid, linolenic acid, and other fatty acids, or combinations thereof.

The peroxide value is the number that expresses in milliequivalents of active oxygen the quantity of peroxide contained in 1000 g of the substance as determined by the methods described in the 5th edition of the European Pharmacopoeia, Section 2.5.5.

Unless otherwise indicated, all numbers expressing quantities, ratios, and numerical properties of ingredients, reaction conditions, and so forth used in the specification and claims are to be understood as being modified in all instances by the term "about".

All parts, percentages, ratios, etc. herein are by weight unless indicated otherwise.

As used herein, "a" or "an" or "the" are used interchangeably with "at least one" to mean "one or more" of the listed element.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION

The present invention provides pharmaceutical formulations that include a therapeutically effective amount of an immune response modifier (IRM) compound selected from the group consisting of imidazoquinoline amines, tetrahydroimidazoquinoline amines, imidazopyridine amines, 6,7-fused cycloalkylimidazopyridine amines, 1,2-bridged imidazoquinoline amines, imidazonaphthyridine amines, tetrahydroimidazonaphthyridine amines, oxazoloquinoline amines, thiazoloquinoline amines, oxazolopyridine amines, thiazolopyridine amines, oxazolonaphthyridine amines, thiazolonaphthyridine amines, and 1H-imidazo dimers fused to pyridine amines, quinoline amines, tetrahydroquinoline amines, naphthyridine amines, or tetrahydronaphthyridine amines, and oleic acid, wherein the oleic acid component contains a low amount of polar impurities, especially peroxides. Surprisingly, the stability of such formulations is substantially greater than that of similar formulations containing an IRM compound and oleic acid containing conventional oleic acid with higher amounts of polar impurities such as peroxides, even when the oleic acid component is of compendial grade. Furthermore, the instability problem of these formulations is not eliminated by additional antioxidants.

Through utilization of an oleic acid component containing a very low amount of polar impurities, the subsequent formation of impurities in IRM formulations is significantly reduced as compared to other IRM formulations comprising compendial grades of oleic acid after both the initial measurement (i.e., its measurement when initially formulated) and under accelerated conditions (when stored for at least 4 months at 40° C. and 75% relative humidity), resulting in an increased formulation shelf life.

For certain embodiments, the formulation comprises an IRM compound and a pharmaceutically acceptable vehicle including an oleic acid component, wherein the formulation is substantially free of polar impurities introduced by the oleic acid component. For certain embodiments, the formulation comprises an IRM compound and a pharmaceutically acceptable vehicle including an oleic acid component, wherein the oleic acid component has a peroxide value no greater than 5. For certain embodiments, the formulation comprises an IRM compound and a pharmaceutically acceptable vehicle including an oleic acid component, wherein the oleic acid component is at least 80% oleic acid.

In certain embodiments, formulations described herein can be in the form of an oil-in-water emulsion such as a cream or a lotion. The oil component of the formulation includes an IRM compound and one or more fatty acids, including oleic acid in an amount sufficient to solubilize the IRM compound. Optionally, a cream or lotion of the invention can contain emollients, antioxidants, emulsifiers, viscosity enhancing agents, and/or preservatives. Such components, as well as all others of the formulations described herein, are preferably pharmaceutically acceptable.

Immune Response Modifying Compounds

Formulations of the invention include an IRM compound. Such compounds include, for example, imidazoquinoline amines including, but not limited to, substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, 6-, 7-, 8-, or 9-aryl, heteroaryl, aryloxy or arylalkyleneoxy substituted imidazoquinoline amines, and imidazoquinoline diamines; tetrahydroimidazoquinoline amines including, but not limited to, amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, thioether substituted tetrahydroimidazoquinoline amines, and tetrahydroquinoline diamines; imidazopyridine amines including, but not limited to, amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, or tetrahydronaphthyridine amines.

These immune response modifier compounds are disclosed in, e.g., U.S. Pat. Nos. 4,689,338; 4,929,624; 5,266,575; 5,268,376; 5,346,905; 5,352,784; 5,389,640; 5,446,153; 5,482,936; 5,756,747; 6,110,929; 6,194,425; 6,331,539; 6,376,669; 6,451,810; 6,525,064; 6,541,485; 6,545,016; 6,545,017; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; 6,756,382; U.S. Patent Publication Nos. 2004/0091491; 2004/0132766; 2004/0147543; and 2004/0176367; and International Patent Application No. PCT/US04/28021 filed on Aug. 27, 2004.

For certain of these embodiments, the IRM compound is an imidazonaphthyridine amine. For certain of these embodiments, the IRM compound is 2-methyl-1-(2-methylpropyl)-1H-imidazo[4,5-c][1,5]naphthyridin-4-amine. For certain of these embodiments, the IRM compound is an imidazoquinoline amine. For certain of these embodiments, the IRM compound is 1-(2-methylpropyl)-1H-imidazo[4,5-c]quinolin-4-amine (imiquimod). For some embodiments, the IRM may have low solubility in water, for example less than about 1 ug/mL (e.g., 0.79 ug/mL in the case of imiquimod), making them difficult to solubilize in aqueous formulations, and potentially using relatively large amounts of oleic acid in the formulation.

The amount of IRM compound that will be therapeutically effective in a specific situation will depend on such things as the activity of the particular compound, the dosing regimen, the application site, the particular formulation and the condition being treated. As such, it is generally not practical to identify specific administration amounts herein; however, those skilled in the art will be able to determine appropriate therapeutically effective amounts based on the guidance provided herein, information available in the art pertaining to IRM compounds, and routine testing. The term "a therapeutically effective amount" means an amount of the IRM compound sufficient to induce a therapeutic or prophylactic effect, such as cytokine induction, inhibition of TH2 immune response, antiviral or antitumor activity, reduction or elimination of postsurgical scarring, reduction or resolution of actinic keratosis or pre-actinic keratosis lesions, reduction in the recurrence of actinic keratosis, treatment of basal cell carcinoma, genital warts, peri-anal warts, molloscum contagiosum, or protection against uv-induced epidermal neoplasia.

In general, the amount of IRM compound present in a topical formulation of the invention will be an amount effective to treat a targeted condition, to prevent recurrence of the condition, or to promote immunity against the condition. In certain embodiments, the amount or concentration of IRM compound is at least 3% by weight, such as, for example, at least 5%, and at least 10%, by weight based on the total weight of the formulation. In other embodiments, the amount of IRM compound is at most 10% by weight, such as, for example, at most 5%, at most 3%, by weight based on the total weight of the formulation. In certain embodiments, the amount or concentration of IRM compound is at least 0.02% by weight, such as, for example, at least 0.03%, at least 0.10%, and at least 0.30% by weight based on the total weight of the formulation.

Fatty Acids

The topical formulations of the invention include fatty acids. In particular, the topical formulations of the invention contain an oleic acid component. As used herein, the term "fatty acid" means a carboxylic acid, either saturated or unsaturated having 6 to 28 carbon atoms, such as, for example, from 10 to 22 carbon atoms.

The fatty acids, including the oleic acid component, may be present in the formulation in an amount sufficient to solubilize the IRM compound. In certain embodiments, the amount of oleic acid component is at least 0.05% by weight, at least 1.0% by weight, at least 3.0% by weight, at least 5.0%, at least 10%, at least 15%, or at least 25%, based on the total weight of the formulation. In certain embodiments, the amount of oleic acid component is at most 40% by weight, at most 30% by weight, at most 15% by weight, or at most 10%, based on the total weight of the formulation.

Compendial grade oleic acid typically contains from 65 to 88 percent (Z)-octadec-9-enoic acid (oleic acid) together with varying amounts of saturated and other unsaturated fatty acids. The composition of fatty acids is determined by gas chromatography using the method described in European Pharmacopeia monograph 01/2005:0799.

For certain embodiments, the oleic acid component contains at least 50%, at least 60%, at least 70% or at least 80% oleic acid. For certain embodiments, the oleic acid component contains at least 80% oleic acid.

For certain embodiments, the oleic acid component is substantially free of polar impurities, such as peroxides. For certain embodiments, the oleic acid component contains less than 10%, less than 5%, less than 1%, or less than 0.1% by weight of polar impurities. For certain embodiments, the oleic acid component has a peroxide value less than 10. For certain embodiments, the oleic acid component has a peroxide value less than 5.

For certain embodiments, the oleic acid component comprises SUPER REFINED Oleic Acid NF, available from Croda Inc., Edison, N.J., USA.

For certain embodiments, the topical formulations of the invention can include fatty acids in addition to those included in the oleic acid component. For example, certain embodiments can include isostearic acid. In some embodiments, the total amount of fatty acids, including those in the oleic acid component, is at least 0.05% by weight, at least 1.0% by weight, at least 3.0% by weight, at least 5.0%, at least 10%, at least 15%, or at least 25%, based on the total weight of the formulation. In certain embodiments, the total amount of fatty acids, including those in the oleic acid component, is at most 40% by weight, at most 30% by weight, at most 15% by weight, or at most 10%, based on the total weight of the formulation.

Antioxidants

For certain embodiments, the topical formulations of the invention can include an antioxidant.

Suitable antioxidants are those that are pharmaceutically acceptable and described in the International Cosmetic Ingredient Dictionary and Handbook, Ninth Edition, Volume 4, 2002, and in the USP NF 2004: The United States Pharmacopeia, 27$^{th}$ Revision and The National Formulary, 22$^{nd}$ Edition.

Examples of suitable antioxidants include ascorbic acid (D and/or L enantiomers), ascorbyl palmitate (D and/or L enantiomers), butylated hydroxyanisole (BHA), butylated hydroxytoluene (BHT), cysteine (D and/or L enantiomers), propyl gallate, sodium formaldehyde sulfoxylate, sodium thiosulfate, and tocopherol.

For certain embodiments, the antioxidant is selected from the group comprising aromatic hydroxy groups capable of hydrogen atom donation. Examples of such antioxidants include BHA, BHT, propyl gallate, and tocopherol.

For certain embodiments, the antioxidant is selected from the group consisting of BHA, BHT, and combinations thereof. For certain embodiments, the antioxidant is BHA.

Preservative System

The formulation often will include a preservative system. The preservative system includes one or more compounds that inhibit microbial growth (e.g., fungal and bacterial growth) within the formulation (for example, during manufacturing and use). The preservative system will generally include at least one preservative compound, such as, for example, methylparaben, ethylparaben, propylparaben, butylparaben, benzyl alcohol, phenoxyethanol, and sorbic acid or derivatives of sorbic acid such as esters and salts. Various combinations of these compounds can be included in the preservative system. In some embodiments of the invention, the preservative system includes methylparaben, propylparaben and benzyl alcohol.

In some embodiments of the invention, the preservative compound is present in an amount of at least 0.01% by weight, such as for example, at least 0.02%, at least 0.03%, at least 0.04%, and at least 0.05%, by weight based on the total weight of the formulation. In other embodiments of the invention the preservative compound is present in an amount of at most 3%, such as for example, at most 2.5%, at most 2.0%, at most 1.0%, at most 0.5%, at most 0.4%, at most 0.3%, and at most 0.2%, by weight based on the total weight of the formulation.

Emollients

The topical formulations of the invention may also include at least one emollient. Examples of useful emollients include but are not limited to long chain alcohols, for example, cetyl alcohol, stearyl alcohol, cetearyl alcohol; fatty acid esters, for example, isopropyl mysristate, isopropyl palmitate, diisopropyl dimer dilinoleate; medium-chain (e.g., 8 to 14 carbon atoms) triglycerides, for example, caprylic/capric triglyceride; cetyl esters; hydrocarbons of 8 or more carbon atoms, for example, light mineral oil, white petrolatum; and waxes, for example, beeswax. Various combinations of such emollients can be used if desired.

In certain embodiments, the amount of the emollient is at least 1.0% by weight, at least 3.0% by weight, at least 5.0% by weight, or at least 10% by weight, based on the total weight of the formulation. In certain embodiments, the amount of emollient is at most 30% by weight, at most 15% by weight, or at most 10% by weight, based on the total weight of the formulation.

Formulations intended for dermal or topical use typically have amounts of an oil phase and an emollient sufficient to provide desirable qualities such as spreadability and feel.

Viscosity Enhancing Agent

The formulations of the present invention can also comprise a viscosity-enhancing agent. Examples of suitable viscosity enhancing agents include long chain alcohols, for example, cetyl alcohol, stearyl alcohol, cetearyl alcohol; cellulose ethers such as hydroxypropylmethylcellulose, hydroxyethylcellulose, hydroxypropylcellulose, and carboxymethylcellulose; polysaccharide gums such as xanthan gum; and homopolymers and copolymers of acrylic acid crosslinked with allyl sucrose or allyl pentaerythriol such as those polymers designated as carbomers in the United States Pharmacopoeia. Suitable carbomers include, for example, those available as CARBOPOL 934P, CARBOPOL 971P, CARBOPOL 940, CARBOPOL 974P, CARBOPOL 980, and PEMULEN TR-1 (USP/NF Monograph; Carbomer 1342), all available from Noveon, Cleveland, Ohio.

In certain embodiments, the amount of the viscosity enhancing agent, when used, is at least 0.1% by weight, at least 0.2% by weight, at least 0.5% by weight, at least 0.6% by weight, at least 0.7% by weight, at least 0.9% by weight, or at least 1.0% by weight, based on the total weight of the formulation. In certain embodiments, the amount of the viscosity-enhancing agent, when used, is at most 10% by weight, at most 5.0% by weight, at most 3.0% by weight, at most 2.0% by weight, or at most 1.5% by weight, based on the total weight of the formulation.

Emulsifier

The formulations of the invention can additionally comprise an emulsifier. Suitable emulsifiers include non-ionic surfactants such as, for example, polysorbate 60, sorbitan monostearate, polyglyceryl-4 oleate, polyoxyethylene(4) lauryl ether, etc. In certain embodiments, the emulsifier is chosen from poloxamers (e.g., PLURONIC F68, also known as POLOXAMER 188, a poly(ethylene glycol)-block-poly(propylene glycol)-block-poly(ethylene glycol), available from BASF, Ludwigshafen, Germany) and sorbitan trioleate (e.g., SPAN 85 available from Uniqema, New Castle, Del.).

If included, the emulsifier is generally present in an amount of 0.1% to 10% by weight of total formulation weight, for example, from 0.5% to 5.0% by weight, and from 0.75% to 4.0% by weight. In certain embodiments, the amount of the emulsifier, if used, is present in an amount of at least 0.1% by weight, at least 0.5% by weight, at least 0.75% by weight, at least 1.0% by weight, at least 2.5% by weight, at least 3.5% by weight, at least 4.0% by weight, or at least 5.0% by weight, based on the total weight of the formulation. In certain embodiments, the amount of the emulsifier, if used, is present in an amount of at most 10% by weight, at most 5.0% by weight, or at most 3.5% by weight, based on the total weight of the formulation.

Some formulations of the invention are oil-in-water emulsions. The water used in these formulations is typically purified water Optionally, a formulation of the invention can contain additional pharmaceutically acceptable excipients such as humectants, such as for example, glycerin; chelating agents, such as for example, ethylenediaminetetraacetic acid; and pH adjusting agents, such as for example, potassium hydroxide or sodium hydroxide.

In some instances, a single ingredient can perform more than one function in a formulation. For example, cetyl alcohol can serve as both an emollient and a viscosity enhancer.

Illustrative Formulation

In one embodiment of the present invention, a pharmaceutical formulation includes:

5% by weight of 1-(2-methylpropyl)-1H-imidazo[4,5-c]quinolin-4-amine;
28% by weight SUPER REFINED oleic acid;
2.2% by weight cetyl alcohol;
3.1% by weight stearyl alcohol;
3% by weight petrolatum;
3.4% by weight polysorbate 60;
0.6% by weight sorbitan monostearate;
2% by weight glycerin;
0.2% by weight methyl hydroxybenzoate;
0.02% by weight propyl hydroxybenzoate;
0.5% by weight xanthan gum;
2% by weight of benzyl alcohol; and
49.98% by weight water;
wherein the weight percentages are based on the total weight of the formulation.

Methods of Application

Formulations according to the present invention can be applied to any suitable location, for example topically to dermal and/or mucosal surfaces. In the case of dermal application, for example, depending on the IRM compound concentration, formulation composition, and dermal surface, the therapeutic effect of the IRM compound may extend only to the superficial layers of the dermal surface or to tissues below the dermal surface. Thus, another aspect of the present invention is directed to a method for the treatment of a dermal and/or mucosal associated condition comprising applying to skin one of the foregoing formulations. As used herein, a "dermal and/or mucosal associated condition" means an inflammatory, infectious, neoplastic or other condition that involves a dermal and/or mucosal surface or that is in sufficient proximity to a dermal and/or mucosal surface to be affected by a therapeutic agent topically applied to the surface. Examples of a dermal and/or mucosal associated condition include warts, atopic dermatitis, postsurgical scars, lesions caused by a herpes virus, and epidermal neoplasias, such as for example actinic keratosis, pre-actinic keratosis lesions, malignant melanomas, basal cell carcinoma, and squamous cell carcinoma.

In one embodiment, the formulations can be applied to the surface of skin for treatment of actinic keratosis (AK). Actinic keratosis are premalignant lesions considered biologically to be either carcinoma in-situ or squamous intraepidermal neoplasia. AK is the most frequent epidermal tumor and is induced by ultraviolet (UV) radiation, typically from sunlight. Because of its precancerous nature, AK may be considered the most important manifestation of sun-induced skin damage.

In some embodiments, the above-described formulations are particularly advantageous for dermal and/or mucosal application for a period of time sufficient to obtain a desired therapeutic effect without undesired systemic absorption of the IRM compound.

EXAMPLES

The following Examples are provided to further describe various formulations and methods according to the invention. The examples, however, are not intended to limit the formulations and methods within the spirit and scope of the invention.

Test Method

A reversed phase high performance liquid chromatography (HPLC) method was used to determine the amount of impurities in cream formulations containing oleic acid.

HPLC parameters: Analytical column: ZORBAX RX C8, 5 micron particle, 15.0×0.46 cm, (available from Agilent Technologies, Wilmington, Del., USA); Detector: UV at 308 nm; Mobile phase: gradient mixture of aqueous ammonium phosphate buffer (prepared by combining 5.1 mL of orthophosphoric acid with 985 mL of water and then adjusting to pH 2.5 with concentrated ammonium hydroxide) and acetonitrile; Gradient: start run at 10% acetonitrile, zero initial hold time, then linear gradient to 70% acetonitrile over 15 minutes, zero final hold time; Flow rate: 2.0 mL/minute; Injection volume: 200 μL; Run time: 15 minutes.

Sample solution: A portion (about 300 mg) of the cream formulation was accurately weighed into a volumetric flask (100 mL). Diluent (50 to 60 mL, prepared by combining 250 parts of acetonitrile, 740 parts of water and 10 parts of hydrochloric acid, all parts by volume) was added to the flask. The flask was vortexed until the cream was completely dispersed and then sonicated for a minimum of 5 minutes. The solution was allowed to cool to ambient temperature and then diluted to volume with diluent and mixed. A portion of the solution was filtered using a syringe equipped with a 0.45 micron polypropylene or polytetralfluoroethylene filter to provide the sample solution.

Preparation of Cream Formulations

The cream formulations in Table 1 below were prepared using the following method.

Water phase preparation: A paraben premix was prepared by combining methyl hydroxybenzoate (methylparaben), propyl hydroxybenzoate (propylparaben), and water; heating the mixture with stirring until the parabens were dissolved; and then allowing the resulting solution to cool to ambient temperature. Glycerin was added to the premix and the mixture was heated to 55±5° C. Xanthan gum was slowly added with mixing. Mixing with heating was continued until the xanthan gum was dispersed.

Oil phase preparation: An imiquimod/oleic acid premix was prepared by combining imiquimod and the oleic acid and then stirring at ambient temperature overnight. Petrolatum, cetyl alcohol, stearyl alcohol, polysorbate 60, sorbitan monostearate, and butylated hydroxyanisole (BHA), if included, were added to the premix. The oil phase was then heated with stirring to 55±5° C. Benzyl alcohol was added to the oil phase just prior to phase combination.

Phase combination: Both phases were removed from their heat source. The aqueous phase was added to the oil phase and the emulsion was homogenized at high speed for at least 5 minutes. The cream was placed in an ice/water bath while homogenizing and homogenization was continued until the temperature of the cream was 35° C. The homogenizer speed was reduced and homogenization was continued until the temperature of the cream was 25° C.

Table 1 summarizes creams A-D in percentage weight-by-weight basis. The formulations were packaged in glass containers.

TABLE 1

| Ingredient | A | B | C | D |
|---|---|---|---|---|
| [1]Imiquimod | 5 | 5 | 5 | 5 |
| [2]Oleic acid, NF | 28 | 28 | — | — |
| [3]SUPER REFINED oleic acid, NF | — | — | 28 | 28 |
| Cetyl alcohol | 2.2 | 2.2 | 2.2 | 2.2 |
| Stearyl alcohol | 3.1 | 3.1 | 3.1 | 3.1 |
| Petrolatum | 3 | 3 | 3 | 3 |
| Polysorbate 60 | 3.4 | 3.4 | 3.4 | 3.4 |
| Sorbitan monostearate | 0.6 | 0.6 | 0.6 | 0.6 |
| Benzyl alcohol | 2 | 2 | 2 | 2 |
| BHA | — | 1 | — | 1 |
| Glycerin | 2 | 2 | 2 | 2 |
| Methylparaben | 0.2 | 0.2 | 0.2 | 0.2 |
| Propylparaben | 0.02 | 0.02 | 0.02 | 0.02 |
| Xanthan gum | 0.5 | 0.5 | 0.5 | 0.5 |
| Water | qs 100 | qs 100 | qs 100 | qs 100 |

[1]1-(2-methylpropyl)-1H-imidazo[4,5-c]quinolin-4-amine
[2]J. T. Baker, a division of Mallinckrodt Baker, Inc, Phillipsburg, NJ, USA
[3]Croda, Inc, Edison, NJ, USA One set of containers was stored at ambient conditions; the samples used to determine initial values came from these containers. The remaining containers were stored in a constant temperature and humidity chamber at 40° C. at 75% relative humidity. At selected time points, containers were removed from the chamber and then stored at ambient conditions until analyzed. Samples were analyzed using the test method described above for impurities. At the 2, 4, and 6 month time points samples were taken from both the top and the bottom of the containers. The results are shown in Table 2 below where each value is the result of a single determination.

Values are not normalized for weight loss that may have occurred during storage.

TABLE 2

| | Impurities (% wt/wt) | | | |
|---|---|---|---|---|
| Timepoint | A | B | C | D |
| [1]Initial - top | 0.09 | 0.08 | 0.02 | 0.03 |
| [2]2 months - top | 0.25 | 0.32 | 0.07 | 0.09 |
| [2]2 months - bottom | 0.33 | 0.30 | 0.04 | 0.15 |
| [3]4 months - top | 0.42 | 0.76 | 0.18 | 0.15 |

TABLE 2-continued

| Timepoint | Impurities (% wt/wt) | | | |
|---|---|---|---|---|
| | A | B | C | D |
| [3]4 months - bottom | 0.46 | 0.56 | 0.04 | 0.29 |
| [4]6 months - top | 0.81 | 0.30 | 0.07 | 0.14 |
| [4]6 months - bottom | 0.49 | 0.29 | 0.04 | 0.07 |

[1]Creams A, B, C, and D were analyzed 16 days, 15 days, 14 days, and 15 days respectively after they were prepared.
[2]All samples were analyzed 10 days after the containers were removed from the constant temperature and humidity chamber.
[3]All samples were analyzed 12 days after the containers were removed from the constant temperature and humidity chamber.
[4]All samples were analyzed 7 days after the containers were removed from the constant temperature and humidity chamber.

The complete disclosures of the patents, patent documents and publications cited herein are incorporated by reference in their entirety as if each were individually incorporated. In case of conflict, the present specification, including definitions, shall control. Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What is claimed is:

1. A pharmaceutical cream formulated with 1-(2-methylpropyl)-1H imidazo[4,5-c]quinolin-4-amine (imiquimod) for topical application to a dermal or mucosal surface to treat a dermal and/or mucosal associated condition, said pharmaceutical cream comprising:
   a therapeutically effective amount of imiquimod; and
   a pharmaceutically acceptable vehicle including an oleic acid component, wherein said oleic acid component contains at least about 80% oleic acid by weight as a fatty acid and has a peroxide value of no more than about 5 milliequivalents of oxygen per kilogram and contains less than about 1% by weight polar impurities at or prior to formulation of said pharmaceutical cream.

2. The pharmaceutical cream of claim 1, wherein the pharmaceutical cream further comprises an antioxidant.

3. The pharmaceutical cream of claim 1, wherein said pharmaceutical cream further comprises an antioxidant selected from the group consisting of butylated hydroxyl toluene (BHT) and butylated hydroxyanisole (BHA).

4. The pharmaceutical cream of claim 1, wherein the imiquimod is present in an amount of not more than 10% by weight based on the total weight of said pharmaceutical cream.

5. The pharmaceutical cream of claim 1, wherein the imiquimod is present in an amount of not more than 5% by weight based on the total weight of said pharmaceutical cream.

6. The pharmaceutical cream of claim 1, wherein the imiquimod is present in an amount of not more than 3% by weight based on the total weight of said pharmaceutical cream.

7. The pharmaceutical cream of claim 1, wherein the oleic acid component is present in an amount of no more than about 10% by weight based on the total weight of said pharmaceutical cream.

8. The pharmaceutical cream of claim 1, wherein the oleic acid component is present in an amount of no more than about 15% by weight based on the total weight of said pharmaceutical cream.

9. The pharmaceutical cream of claim 1, wherein the oleic acid component is present in an amount of no more than about 30% by weight based on the total weight of said pharmaceutical cream.

10. The pharmaceutical cream of claim 1, wherein the oleic acid component is present in an amount of no more than about 40% by weight based on the total weight of said pharmaceutical cream.

11. The pharmaceutical cream of claim 1, wherein the oleic acid component is present in an amount of about 28% by weight based on the total weight of said pharmaceutical cream.

12. The pharmaceutical cream of claim 1, wherein the pharmaceutical cream includes at least one additional fatty acid other than the oleic acid.

13. The pharmaceutical cream of claim 1, wherein the pharmaceutical cream further includes isostearic acid.

14. The pharmaceutical cream of claim 1, wherein the pharmaceutical cream includes less than 3% isostearic acid by weight based upon the total weight of the pharmaceutical cream.

15. The pharmaceutical cream of claim 1, wherein the imiquimod is present in an amount of not more than 10% by weight based on the total weight of said pharmaceutical cream and wherein the oleic acid component is present in an amount of no more than about 40% by weight based on the total weight of said pharmaceutical cream.

16. The pharmaceutical cream of claim 1, wherein the imiquimod is present in an amount of about 5% by weight based on the total weight of said pharmaceutical cream and wherein the oleic acid component is present in an amount of about 28% by weight based on the total weight of said pharmaceutical cream.

17. The pharmaceutical cream of claim 1, wherein the pharmaceutical cream further comprises water.

18. The pharmaceutical cream of claim 1, wherein the pharmaceutical cream further comprises a preservative system.

19. The pharmaceutical cream of claim 1, wherein the pharmaceutical cream further comprises an emulsifier.

20. The pharmaceutical cream of claim 1, wherein the dermal and/or mucosal associated condition is an epidermal neoplasia.

21. The pharmaceutical cream of claim 1, wherein the dermal and/or mucosal associated condition is actinic keratosis.

22. The pharmaceutical cream of claim 1, wherein the dermal and/or mucosal associated condition is pre-actinic keratosis.

23. The pharmaceutical cream of claim 1, wherein the dermal and/or mucosal associated condition is warts.

24. The pharmaceutical cream of claim 1, wherein the dermal and/or mucosal associated condition is peri-anal warts.

25. The pharmaceutical cream of claim 1, wherein the dermal and/or mucosal associated condition is genital warts.

26. The pharmaceutical cream of claim 1, wherein the dermal and/or mucosal associated condition is peri-anal or genital warts.

27. The pharmaceutical cream of claim 1, wherein the dermal and/or mucosal associated condition is basal cell carcinoma.

28. The pharmaceutical cream of claim 1, wherein the dermal and/or mucosal associated condition is molloscum contagiosum.

29. The pharmaceutical cream of claim 1, wherein the dermal and/or mucosal associated condition is a malignant melanoma.

30. The pharmaceutical cream of claim 1, wherein the dermal and/or mucosal associated condition is squamous cell carcinoma.

31. The pharmaceutical cream of claim 1, wherein the dermal and/or mucosal associated condition is atopic dermatitis.

32. The pharmaceutical cream of claim 1, wherein the dermal and/or mucosal associated condition is post surgical scars.

33. The pharmaceutical cream of claim 1, wherein the dermal and/or mucosal associated condition is a lesion caused by a herpes virus.

34. A pharmaceutical cream formulated with 1-(2-methylpropyl)-1H imidazo[4,5-c]quinolin-4-amine (imiquimod) for topical application to a dermal or mucosal surface to treat a dermal and/or mucosal associated condition, said pharmaceutical cream comprising:
    imiquimod in an amount of not more than 5% by weight based on the total weight of said pharmaceutical cream; and
    a pharmaceutically acceptable vehicle including an oleic acid component, wherein said oleic acid component contains at least about 80% oleic acid by weight as a fatty acid and has a peroxide value of no more than about 5 milliequivalents of oxygen per kilogram and contains less than about 1% by weight polar impurities at or prior to formulation of said pharmaceutical cream, and wherein the oleic acid component is present in an amount of no more than about 30% by weight based on the total weight of said pharmaceutical cream.

35. The pharmaceutical cream of claim 34, wherein the pharmaceutical cream further comprises an antioxidant.

36. The pharmaceutical cream of claim 35, wherein said pharmaceutical cream further comprises an antioxidant selected from the group consisting of butylated hydroxyl toluene (BHT) and butylated hydroxyanisole (BHA).

37. The pharmaceutical cream of claim 34, wherein the pharmaceutical cream includes at least one additional fatty acid other than the oleic acid.

38. The pharmaceutical cream of claim 37, wherein the additional fatty acid is isostearic acid.

39. A pharmaceutical cream formulated with 1-(2-methylpropyl)-1H imidazo[4,5-c]quinolin-4-amine (imiquimod) for topical application to a dermal or mucosal surface to treat a dermal and/or mucosal associated condition, said pharmaceutical cream comprising:
    imiquimod in an amount of not more than 10% by weight based on the total weight of said pharmaceutical cream; and
    a pharmaceutically acceptable vehicle including an oleic acid component, wherein said oleic acid component contains at least about 80% oleic acid by weight as a fatty acid and has a peroxide value of no more than about 5 milliequivalents of oxygen per kilogram and contains less than about 1% by weight polar impurities at or prior to formulation of said pharmaceutical cream, and wherein the oleic acid component is present in an amount of no more than about 40% by weight based on the total weight of said pharmaceutical cream.

40. The pharmaceutical cream of claim 39, wherein the pharmaceutical cream further comprises an antioxidant.

41. The pharmaceutical cream of claim 40, wherein said pharmaceutical cream further comprises an antioxidant selected from the group consisting of butylated hydroxyl toluene (BHT) and butylated hydroxyanisole (BHA).

42. The pharmaceutical cream of claim 39, wherein the pharmaceutical cream includes at least one additional fatty acid other than the oleic acid.

43. The pharmaceutical cream of claim 42, wherein the additional fatty acid is isostearic acid.

44. A pharmaceutical cream formulated with 1-(2-methylpropyl)-1H imidazo[4,5-c]quinolin-4-amine (imiquimod) for topical application to a dermal or mucosal surface to treat a dermal and/or mucosal associated condition, said pharmaceutical cream comprising:
    imiquimod in an amount of not more than 5% by weight based on the total weight of said pharmaceutical cream; and
    a pharmaceutically acceptable vehicle including an oleic acid component, wherein said oleic acid component contains at least about 80% oleic acid by weight as a fatty acid and has a peroxide value of no more than about 5 milliequivalents of oxygen per kilogram and contains less than about 1% by weight polar impurities at or prior to formulation of said pharmaceutical cream, and wherein the oleic acid component is present in an amount of about 25% by weight based on the total weight of said pharmaceutical cream.

45. The pharmaceutical cream of claim 44, wherein the pharmaceutical cream further comprises an antioxidant.

46. The pharmaceutical cream of claim 45, wherein said pharmaceutical cream further comprises an antioxidant selected from the group consisting of butylated hydroxyl toluene (BHT) and butylated hydroxyanisole (BHA).

47. The pharmaceutical cream of claim 44, wherein the pharmaceutical cream includes at least one additional fatty acid other than the oleic acid.

48. The pharmaceutical cream of claim 47, wherein the additional fatty acid is isostearic acid.

49. A pharmaceutical cream formulated with 1-(2-methylpropyl)-1H imidazo[4,5-c]quinolin-4-amine (imiquimod) for topical application to a dermal or mucosal surface to treat a dermal and/or mucosal associated condition, said pharmaceutical cream comprising:
    imiquimod in an amount of not more than 5% by weight based on the total weight of said pharmaceutical cream; and
    a pharmaceutically acceptable vehicle including an oleic acid component, wherein said oleic acid component contains at least about 80% oleic acid by weight as a fatty acid and has a peroxide value of no more than about 5 milliequivalents of oxygen per kilogram and contains less than about 1% by weight polar impurities at or prior to formulation of said pharmaceutical cream, and wherein the oleic acid component is present in an amount of no more than about 10% by weight based on the total weight of said pharmaceutical cream.

50. The pharmaceutical cream of claim 49, wherein the pharmaceutical cream further comprises an antioxidant.

51. The pharmaceutical cream of claim 50, wherein said pharmaceutical cream further comprises an antioxidant selected from the group consisting of butylated hydroxyl toluene (BHT) and butylated hydroxyanisole (BHA).

52. The pharmaceutical cream of claim 49, wherein the pharmaceutical cream includes at least one additional fatty acid other than the oleic acid.

53. The pharmaceutical cream of claim 52, wherein the additional fatty acid is isostearic acid.

54. The pharmaceutical cream of claim 1, wherein the oleic acid component is present in an amount of about 25% by weight based on the total weight of said pharmaceutical cream.

55. The pharmaceutical cream of claim 1, wherein the imiquimod is present in an amount of about 5% by weight based on the total weight of said pharmaceutical cream and wherein the oleic acid component is present in an amount of about 25% by weight based on the total weight of said pharmaceutical cream.

56. A pharmaceutical cream formulated with 1-(2-methylpropyl)-1H imidazo[4,5-c]quinolin-4-amine (imiquimod) for topical application to a dermal or mucosal surface to treat a dermal and/or mucosal associated condition, said pharmaceutical cream comprising:
a therapeutically effective amount of imiquimod;
a pharmaceutically acceptable vehicle including an oleic acid component, wherein said oleic acid component contains at least about 80% oleic acid by weight as a fatty acid and has a peroxide value of no more than about 5 milliequivalents of oxygen per kilogram and contains less than about 1% by weight polar impurities at or prior to formulation of said pharmaceutical cream; and
water.

57. A pharmaceutical cream formulated with 1-(2-methylpropyl)-1H imidazo[4,5-c]quinolin-4-amine (imiquimod) for topical application to a dermal or mucosal surface to treat a dermal and/or mucosal associated condition, said pharmaceutical cream comprising:
a therapeutically effective amount of imiquimod;
a pharmaceutically acceptable vehicle including an oleic acid component, wherein said oleic acid component contains at least about 80% oleic acid by weight as a fatty acid and has a peroxide value of no more than about 5 milliequivalents of oxygen per kilogram and contains less than about 1% by weight polar impurities at or prior to formulation of said pharmaceutical cream; and
a preservative.

58. A pharmaceutical cream formulated with 1-(2-methylpropyl)-1H imidazo[4,5-c]quinolin-4-amine (imiquimod) for topical application to a dermal or mucosal surface to treat a dermal and/or mucosal associated condition, said pharmaceutical cream comprising:
a therapeutically effective amount of imiquimod;
a pharmaceutically acceptable vehicle including an oleic acid component, wherein said oleic acid component contains at least about 80% oleic acid by weight as a fatty acid and has a peroxide value of no more than about 5 milliequivalents of oxygen per kilogram and contains less than about 1% by weight polar impurities at or prior to formulation of said pharmaceutical cream; and
an emulsifier.

59. A pharmaceutical cream formulated with 1-(2-methylpropyl)-1H imidazo[4,5-c]quinolin-4-amine (imiquimod) for topical application to a dermal or mucosal surface to treat a dermal and/or mucosal associated condition, said pharmaceutical cream comprising:
a therapeutically effective amount of imiquimod; and
a pharmaceutically acceptable vehicle including an oleic acid component, wherein said oleic acid component contains at least about 80% oleic acid by weight as a fatty acid and has a peroxide value of no more than about 5 milliequivalents of oxygen per kilogram and contains less than about 1% by weight polar impurities at or prior to formulation of said pharmaceutical cream,
wherein the dermal and/or mucosal associated condition is actinic keratosis.

60. A pharmaceutical cream formulated with 1-(2-methylpropyl)-1H imidazo[4,5-c]quinolin-4-amine (imiquimod) for topical application to a dermal or mucosal surface to treat a dermal and/or mucosal associated condition, said pharmaceutical cream comprising:
a therapeutically effective amount of imiquimod; and
a pharmaceutically acceptable vehicle including an oleic acid component, wherein said oleic acid component contains at least about 80% oleic acid by weight as a fatty acid and has a peroxide value of no more than about 5 milliequivalents of oxygen per kilogram and contains less than about 1% by weight polar impurities at or prior to formulation of said pharmaceutical cream,
wherein the dermal and/or mucosal associated condition is peri-anal warts.

61. A pharmaceutical cream formulated with 1-(2-methylpropyl)-1H imidazo[4,5-c]quinolin-4-amine (imiquimod) for topical application to a dermal or mucosal surface to treat a dermal and/or mucosal associated condition, said pharmaceutical cream comprising:
a therapeutically effective amount of imiquimod; and
a pharmaceutically acceptable vehicle including an oleic acid component, wherein said oleic acid component contains at least about 80% oleic acid by weight as a fatty acid and has a peroxide value of no more than about 5 milliequivalents of oxygen per kilogram and contains less than about 1% by weight polar impurities at or prior to formulation of said pharmaceutical cream,
wherein the dermal and/or mucosal associated condition is genital warts.

62. A pharmaceutical cream formulated with 1-(2-methylpropyl)-1H imidazo[4,5-c]quinolin-4-amine (imiquimod) for topical application to a dermal or mucosal surface to treat a dermal and/or mucosal associated condition, said pharmaceutical cream comprising:
a therapeutically effective amount of imiquimod; and
a pharmaceutically acceptable vehicle including an oleic acid component, wherein said oleic acid component contains at least about 80% oleic acid by weight as a fatty acid and has a peroxide value of no more than about 5 milliequivalents of oxygen per kilogram and contains less than about 1% by weight polar impurities at or prior to formulation of said pharmaceutical cream,
wherein the dermal and/or mucosal associated condition is basal cell carcinoma.

63. The pharmaceutical cream of claim 1, wherein said oleic acid component is Super Refined oleic acid NF.

64. The pharmaceutical cream of claim 34, wherein said oleic acid component is Super Refined oleic acid NF.

65. The pharmaceutical cream of claim 39, wherein said oleic acid component is Super Refined oleic acid NF.

66. The pharmaceutical cream of claim 44, wherein said oleic acid component is Super Refined oleic acid NF.

67. The pharmaceutical cream of claim 49, wherein said oleic acid component is Super Refined oleic acid NF.

68. The pharmaceutical cream of claim 56, wherein said oleic acid component is Super Refined oleic acid NF.

69. The pharmaceutical cream of claim 57, wherein said oleic acid component is Super Refined oleic acid NF.

70. The pharmaceutical cream of claim 58, wherein said oleic acid component is Super Refined oleic acid NF.

71. The pharmaceutical cream of claim 59, wherein said oleic acid component is Super Refined oleic acid NF.

72. The pharmaceutical cream of claim 60, wherein said oleic acid component is Super Refined oleic acid NF.

73. The pharmaceutical cream of claim 61, wherein said oleic acid component is Super Refined oleic acid NF.

74. The pharmaceutical cream of claim 62, wherein said oleic acid component is Super Refined oleic acid NF.

75. A pharmaceutical cream formulated with 1-(2-methylpropyl)-1H imidazo[4,5-c]quinolin-4-amine (imiquimod) for topical application to a dermal or mucosal surface of a subject to treat a dermal and/or mucosal associated condition, said pharmaceutical cream comprising:
a therapeutically effective amount of imiquimod; and
a pharmaceutically acceptable vehicle including Super Refined oleic acid NF.

76. The pharmaceutical cream of claim 75, wherein said pharmaceutical cream further comprises an antioxidant.

77. The pharmaceutical cream of claim 76, wherein the antioxidant is selected from a group of antioxidants consisting of butylated hydroxyl toluene (BHT) and butylated hydroxyanisole (BHA).

78. The pharmaceutical cream of claim 75, wherein the imiquimod is present in an amount of at most about 10% by weight based on the total weight of said pharmaceutical cream.

79. The pharmaceutical cream of claim 75, wherein the imiquimod is present in an amount of at most about 5% by weight based on the total weight of said pharmaceutical cream.

80. The pharmaceutical cream of claim 75, wherein the imiquimod is present in an amount of at most about 3% by weight based on the total weight of said pharmaceutical cream.

81. The pharmaceutical cream of claim 75, wherein the Super Refined oleic acid NF is present in an amount of at most about 10% by weight based on the total weight of said pharmaceutical cream.

82. The pharmaceutical cream of claim 75, wherein the Super Refined oleic acid NF is present in an amount of at most about 15% by weight based on the total weight of said pharmaceutical cream.

83. The pharmaceutical cream of claim 75, wherein the Super Refined oleic acid NF is present in an amount of at most about 30% by weight based on the total weight of said pharmaceutical cream.

84. The pharmaceutical cream of claim 75, wherein the Super Refined oleic acid NF is present in an amount of at most about 40% by weight based on the total weight of said pharmaceutical cream.

85. The pharmaceutical cream of claim 75, wherein the Super Refined oleic acid NF is present in an amount of about 28% by weight based on the total weight of said pharmaceutical cream.

86. The pharmaceutical cream of claim 75, wherein the Super Refined oleic acid NF is present in an amount of about 25% by weight based on the total weight of said pharmaceutical cream.

87. The pharmaceutical cream of claim 75, wherein the pharmaceutical cream further comprises water.

88. The pharmaceutical cream of claim 75, wherein the pharmaceutical cream further comprises a preservative system.

89. The pharmaceutical cream of claim 75, wherein the pharmaceutical cream further comprises an emulsifier.

90. The pharmaceutical cream of claim 75, wherein the dermal and/or mucosal associated condition is an epidermal neoplasia.

91. The pharmaceutical cream of claim 75, wherein the dermal and/or mucosal associated condition is actinic keratosis.

92. The pharmaceutical cream of claim 75, wherein the dermal and/or mucosal associated condition is pre-actinic keratosis.

93. The pharmaceutical cream of claim 75, wherein the dermal and/or mucosal associated condition is warts.

94. The pharmaceutical cream of claim 75, wherein the dermal and/or mucosal associated condition is perianal warts.

95. The pharmaceutical cream of claim 75, wherein the dermal and/or mucosal associated condition is genital warts.

96. The pharmaceutical cream of claim 75, wherein the dermal and/or mucosal associated condition is perianal or genital warts.

97. The pharmaceutical cream of claim 75, wherein the dermal and/or mucosal associated condition is basal cell carcinoma.

98. The pharmaceutical cream of claim 75, wherein the dermal and/or mucosal associated condition is molloscum contagiosum.

99. The pharmaceutical cream of claim 75, wherein the dermal and/or mucosal associated condition is a malignant melanoma.

100. The pharmaceutical cream of claim 75, wherein the dermal and/or mucosal associated condition is squamous cell carcinoma.

101. The pharmaceutical cream of claim 75, wherein the dermal and/or mucosal associated condition is atopic dermatitis.

102. The pharmaceutical cream of claim 75, wherein the dermal and/or mucosal associated condition is post surgical scars.

103. The pharmaceutical cream of claim 75, wherein the dermal and/or mucosal associated condition is a lesion caused by a herpes virus.

104. The pharmaceutical cream of claim 75, wherein the pharmaceutical cream further includes:
(a) cetyl alcohol;
(b) stearyl alcohol;
(c) petrolatum;
(d) polysorbate 60;
(e) Sorbitan monostearate;
(f) benzyl alcohol;
(g) glycerin;
(h) methylparaben;
(i) propylparaben;
(j) Xanthan gum; and
(k) water.

105. A pharmaceutical cream formulated with 1-(2-methylpropyl)-1H imidazo[4,5-c]quinolin-4-amine (imiquimod) for topical application to a dermal or mucosal surface of a subject to treat a dermal and/or mucosal associated condition, said pharmaceutical cream comprising:
imiquimod in an amount of at most about 10% by weight based on the total weight of said pharmaceutical cream; and
a pharmaceutically acceptable vehicle including an Super Refined oleic acid NF, wherein the Super Refined oleic acid NF is present in an amount of at most about 40% by weight based on the total weight of said pharmaceutical cream.

106. The pharmaceutical cream of claim 105, wherein the pharmaceutical cream further comprises an antioxidant.

107. The pharmaceutical cream of claim 106, wherein the antioxidant is selected from a group of antioxidants consisting of butylated hydroxyl toluene (BHT) and butylated hydroxyanisole (BHA).

108. The pharmaceutical cream of claim 105, wherein the pharmaceutical cream further includes:
(a) cetyl alcohol;
(b) stearyl alcohol;
(c) petrolatum;
(d) polysorbate 60;
(e) Sorbitan monostearate;
(f) benzyl alcohol;
(g) glycerin;
(h) methylparaben;
(i) propylparaben;
(j) Xanthan gum; and
(k) water.

109. The pharmaceutical cream of claim 105, wherein the dermal and/or mucosal associated condition is selected from a group of dermal and/or mucosal associated conditions consisting of actinic keratosis, pre-actinic keratosis, genital warts, perianal warts and basal cell carcinoma.

110. The pharmaceutical cream of claim 105, wherein the dermal and/or mucosal associated condition is selected from a group of dermal and/or mucosal associated conditions consisting of a wart, molloscum contagiosum, an epidermal neoplasia, a malignant melanoma, a squamous cell carcinoma, atopic dermatitis, a post surgical scar and a lesion caused by a herpes virus.

111. A pharmaceutical cream formulated with 1-(2-methylpropyl)-1H imidazo[4,5-c]quinolin-4-amine (imiquimod) for topical application to a dermal or mucosal surface of a subject to treat a dermal and/or mucosal associated condition, said pharmaceutical cream comprising:
imiquimod in an amount of at most about 5% by weight based on the total weight of said pharmaceutical cream; and
a pharmaceutically acceptable vehicle including an Super Refined oleic acid NF, wherein the Super Refined oleic acid NF is present in an amount of at most about 30% by weight based on the total weight of said pharmaceutical cream.

112. The pharmaceutical cream of claim 111, wherein the pharmaceutical cream further comprises an antioxidant.

113. The pharmaceutical cream of claim 112, wherein the antioxidant is selected from a group of antioxidants consisting of butylated hydroxyl toluene (BHT) and butylated hydroxyanisole (BHA).

114. The pharmaceutical cream of claim 111, wherein the pharmaceutical cream further includes:
(a) cetyl alcohol;
(b) stearyl alcohol;
(c) petrolatum;
(d) polysorbate 60;
(e) Sorbitan monostearate;
(f) benzyl alcohol;
(g) glycerin;
(h) methylparaben;
(i) propylparaben;
(j) Xanthan gum; and
(k) water.

115. The pharmaceutical cream of claim 111, wherein the dermal and/or mucosal associated condition is selected from a group of dermal and/or mucosal associated conditions consisting of actinic keratosis, pre-actinic keratosis, genital warts, perianal warts and basal cell carcinoma.

116. The pharmaceutical cream of claim 111, wherein the dermal and/or mucosal associated condition is selected from a group of dermal and/or mucosal associated conditions consisting of a wart, molloscum contagiosum, an epidermal neoplasia, a malignant melanoma, a squamous cell carcinoma, atopic dermatitis, a post surgical scar and a lesion caused by a herpes virus.

117. A pharmaceutical cream formulated with 1-(2-methylpropyl)-1H imidazo[4,5-c]quinolin-4-amine (imiquimod) for topical application to a dermal or mucosal surface of a subject to treat a dermal and/or mucosal associated condition, said pharmaceutical cream comprising:
imiquimod in an amount of about 5% by weight based on the total weight of said pharmaceutical cream; and
a pharmaceutically acceptable vehicle including an Super Refined oleic acid NF, wherein the Super Refined oleic acid NF is present in an amount of about 28% by weight based on the total weight of said pharmaceutical cream.

118. The pharmaceutical cream of claim 117, wherein the pharmaceutical cream further comprises an antioxidant.

119. The pharmaceutical cream of claim 118, wherein the antioxidant is selected from a group of antioxidants consisting of butylated hydroxyl toluene (BHT) and butylated hydroxyanisole (BHA).

120. The pharmaceutical cream of claim 117, wherein the pharmaceutical cream further includes:
(a) cetyl alcohol;
(b) stearyl alcohol;
(c) petrolatum;
(d) polysorbate 60;
(e) Sorbitan monostearate;
(f) benzyl alcohol;
(g) glycerin;
(h) methylparaben;
(i) propylparaben;
(j) Xanthan gum; and
(k) water.

121. The pharmaceutical cream of claim 117, wherein the dermal and/or mucosal associated condition is selected from a group of dermal and/or mucosal associated conditions consisting of actinic keratosis, pre-actinic keratosis, genital warts, perianal warts and basal cell carcinoma.

122. The pharmaceutical cream of claim 117, wherein the dermal and/or mucosal associated condition is selected from a group of dermal and/or mucosal associated conditions consisting of a wart, molloscum contagiosum, an epidermal neoplasia, a malignant melanoma, a squamous cell carcinoma, atopic dermatitis, a post surgical scar and a lesion caused by a herpes virus.

123. The pharmaceutical cream of claim 120, wherein the dermal and/or mucosal associated condition is selected from a group of dermal and/or mucosal associated conditions consisting of a wart, molloscum contagiosum, an epidermal neoplasia, a malignant melanoma, a squamous cell carcinoma, atopic dermatitis, a post surgical scar and a lesion caused by a herpes virus.

124. A pharmaceutical cream formulated with 1-(2-methylpropyl)-1H imidazo[4,5-c]quinolin-4-amine (imiquimod) for topical application to a dermal or mucosal surface of a subject to treat a dermal and/or mucosal associated condition, said pharmaceutical cream comprising:
imiquimod in an amount of about 5% by weight based on the total weight of said pharmaceutical cream; and
a pharmaceutically acceptable vehicle including an Super Refined oleic acid NF, wherein the Super Refined oleic acid NF is present in an amount of about 28% by weight based on the total weight of said pharmaceutical cream.

125. The pharmaceutical cream of claim 124, wherein the pharmaceutical cream further comprises an antioxidant.

126. The pharmaceutical cream of claim 125, wherein the antioxidant is selected from a group of antioxidants consisting of butylated hydroxyl toluene (BHT) and butylated hydroxyanisole (BHA).

127. The pharmaceutical cream of claim 124, wherein the pharmaceutical cream further includes:
    (a) cetyl alcohol;
    (b) stearyl alcohol;
    (c) petrolatum;
    (d) polysorbate 60;
    (e) Sorbitan monostearate;
    (f) benzyl alcohol;
    (g) glycerin;
    (h) methylparaben;
    (i) propylparaben;
    (j) Xanthan gum; and
    (k) water.

128. The pharmaceutical cream of claim 124, wherein the dermal and/or mucosal associated condition is selected from a group of dermal and/or mucosal associated conditions consisting of actinic keratosis, pre-actinic keratosis, genital warts, perianal warts and basal cell carcinoma.

129. The pharmaceutical cream of claim 124, wherein the dermal and/or mucosal associated condition is selected from a group of dermal and/or mucosal associated conditions consisting of a wart, molloscum contagiosum, an epidermal neoplasia, a malignant melanoma, a squamous cell carcinoma, atopic dermatitis, a post surgical scar and a lesion caused by a herpes virus.

130. The pharmaceutical cream of claim 127, wherein the dermal and/or mucosal associated condition is selected from a group of dermal and/or mucosal associated conditions consisting of a wart, molloscum contagiosum, an epidermal neoplasia, a malignant melanoma, a squamous cell carcinoma, atopic dermatitis, a post surgical scar and a lesion caused by a herpes virus.

131. A pharmaceutical cream formulated with 1-(2-methylpropyl)-1H imidazo[4,5-c]quinolin-4-amine (imiquimod) for topical application to a dermal or mucosal surface of a subject to treat a dermal and/or mucosal associated condition, wherein the dermal and/or mucosal associated condition is selected from a group of dermal and/or mucosal associated conditions consisting of actinic keratosis, genital warts, perianal warts and basal cell carcinoma, said pharmaceutical cream comprising:
    (a) imiquimod in an amount of about 5% by weight based on the total weight of said pharmaceutical cream; and
    (b) a pharmaceutically acceptable vehicle, said vehicle including:
        (i) an Super Refined oleic acid NF, wherein the Super Refined oleic acid NF is present in an amount of about 28% by weight based on the total weight of said pharmaceutical cream;
        (ii) cetyl alcohol;
        (iii) stearyl alcohol;
        (iv) petrolatum;
        (v) polysorbate 60;
        (vi) Sorbitan monostearate;
        (vii) benzyl alcohol;
        (viii) glycerin;
        (ix) methylparaben;
        (x) propylparaben;
        (xi) Xanthan gum; and
        (xii) water.

132. A pharmaceutical cream formulated with 1-(2-methylpropyl)-1H imidazo[4,5-c]quinolin-4-amine (imiquimod) for topical application to a dermal or mucosal surface of a subject to treat a dermal and/or mucosal associated condition, wherein the dermal and/or mucosal associated condition is selected from a group of dermal and/or mucosal associated conditions consisting of actinic keratosis, genital warts, perianal warts and basal cell carcinoma, said pharmaceutical cream comprising:
    (a) imiquimod in an amount of about 5% by weight based on the total weight of said pharmaceutical cream; and
    (b) a pharmaceutically acceptable vehicle, said vehicle including:
        (i) an Super Refined oleic acid NF, wherein the Super Refined oleic acid NF is present in an amount of about 25% by weight based on the total weight of said pharmaceutical cream;
        (ii) cetyl alcohol;
        (iii) stearyl alcohol;
        (iv) petrolatum;
        (v) polysorbate 60;
        (vi) Sorbitan monostearate;
        (vii) benzyl alcohol;
        (viii) glycerin;
        (ix) methylparaben;
        (x) propylparaben;
        (xi) Xanthan gum; and
        (xii) water.

* * * * *